(12) United States Patent
Hong et al.

(10) Patent No.: US 8,119,132 B2
(45) Date of Patent: Feb. 21, 2012

(54) HUMANIZED ANTI-TAG-72 MONOCLONAL ANTIBODIES

(75) Inventors: Hyo Jeong Hong, Daejeon (KR); Sang Jick Kim, Daejeon (KR); Sun Ok Yoon, Daejeon (KR); Myeong Hee Jang, Daejeon (KR); Keun Soo Kim, Daejeon (KR); Tae Sup Lee, Seoul (KR); Chang Woon Choi, Seoul (KR)

(73) Assignee: Korea Research Institute of Bioscience and Biotech, Daejeon (KR)

( * ) Notice: Subject to any disclaimer, the term of this patent is extended or adjusted under 35 U.S.C. 154(b) by 441 days.

(21) Appl. No.: 11/628,423

(22) PCT Filed: May 6, 2005

(86) PCT No.: PCT/KR2005/001322
§ 371 (c)(1),
(2), (4) Date: Apr. 25, 2008

(87) PCT Pub. No.: WO2005/121180
PCT Pub. Date: Dec. 22, 2005

(65) Prior Publication Data
US 2008/0279847 A1    Nov. 13, 2008

(30) Foreign Application Priority Data
Jun. 5, 2004   (KR) .................. 10-2004-0041199

(51) Int. Cl.
*A61K 39/395*   (2006.01)
*C07K 16/18*    (2006.01)
(52) U.S. Cl. .................. 424/133.1; 530/387.3
(58) Field of Classification Search ............... 424/133.1; 530/387.3
See application file for complete search history.

(56) References Cited

U.S. PATENT DOCUMENTS

| 5,976,531 | A  | 11/1999 | Mezes et al. |
| 6,495,137 | B1 | 12/2002 | Mezes et al. |

FOREIGN PATENT DOCUMENTS

| KR | 100162021 B1 |   | 8/1998 |
| KR | 10-2000-0005885 |   | 1/2000 |
| KR | 2003013633 | * | 8/2001 |
| WO | WO 86/01533 |   | 3/1986 |
| WO | WO 88/07085 |   | 9/1988 |
| WO | WO 88/07086 |   | 9/1988 |
| WO | WO 88/09344 |   | 12/1988 |
| WO | WO 99/43816 A1 |   | 9/1999 |
| WO | WO 00/26394 A1 |   | 5/2000 |
| WO | WO 2005/047338 |   | 5/2005 |

OTHER PUBLICATIONS

Vajdos et al. (J. Molec. Biol. 320(2):415-428 (2002)).*
Brummell et al. (Biochemistry 32:1180-1187 (1993)).*
Kobayashi et al. (Protein Engineering 12(10):879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Dufner (Trends Biotechnol. 24(11):523-29 (2006)).*
Voskoglou-Nomikos (Clin. Can. Res. 9:4227-4239 (2003)).*
Dennis (Nature 442:739-741 (2006)).*
Cespdes et al. (Clin. Transl. Oncol. 8(5):318-329 (2006)).*
Talmadge et al. (Am. J. Pathol 170(3):793-804 (2007)).*
Fujimori et al. (J. Nuc. Med. 31:1191-1198 (1990)).*
Beckman et al. (Can. 109:170-179 (2007)).*
Thurber et al. (Adv. Drug Deliv. Rev. 60:1421-1434 (2008)).*
Rudnick et al. (Can. Biotherp. & Radiopharm. 24: 155-162 (2009)).*
Colcher et al, "A spectrum of monoclonal antibodies reactive with human mammary tumor cells," Proc Natl Acad Sci, USA 1981, 78(5) 3199-3203.
Muraro et al, "Generation and Characterization of B72.3 Second Generation Monoclonal Antibodies Reactive with the Tumor-associated Glycoprotein 72 Antigen," Cancer Res, 1988, 48(16): 4588-4596.
Divgi et al, "Clinical Comparison of Radiolocalization of Two Monoclonal Antibodies (mAbs) Against the TAG-72 Antigen," Nucl Med Biol, 1994, 21(1): 9-15.
Owens et al, "The genetic engineering of monoclonal antibodies," J. Immunol methods, 1994, 168(2): 149-65.
Brown et al, "Anti-Tac-H, a humanized antibody to the interleukin 2 receptor, prolongs primate cardiac allograft survival," Proc Natl Acad Sci, USA 1991, 88: 2663.
Kashmiri et al, "Generation,; Characterization, and in Vivo Studies of Humanized Anticarcinoma Antibody CC49," Hybridoma, 1995 14: 461-473.
Jones et al, "Replacing the complementarity determining regions in a human antibody with those from a mouse," Nature, 1986, 4: 321 (6069): 522-525.
Riechmann et al, "Reshaping human antibodies for therapy," Nature, 1988, 332: 323-327.
Queen et al, "A humanized antibody that binds to the interleukin 2 receptor," Proc Natl Acad Sci. USA 1999, 86: 10023-10029.
Tempest et al, "Reshaping a Human Monoclonal Antibody to Inhibit Human Respiutory SYNmIAL Virus Infeoion in Vivo," Biol Technology, 1991, 9: 266-271.
Co et al, "Humanized antibodies for therapy," Nature 1991, 351: 501-502.
Goldenberg et al, "Use of Radiolabeled Antibodies to Carcinoembryonic Antigen for the Detection and Localization of Diverse Cancers by External Photoscanning," New England J Med 1978, 298, 1384-1388.

(Continued)

*Primary Examiner* — Lynn Bristol
(74) *Attorney, Agent, or Firm* — Casimir Jones SC

(57) ABSTRACT

The present invention relates to humanized antibodies specific to a tumor-associated glycoprotein, TAG-72, and anticancer compositions comprising the humanized antibodies. In detail, the present invention relates to a humanized antibody which has enhanced antigen binding affinity by mutating a heavy chain of a humanized antibody PXA/HzK specific for TAG-72, an antibody which is prepared by replacing a light chain of the humanized antibody with a human light chain, and anticancer compositions including the antibodies.

10 Claims, 12 Drawing Sheets

OTHER PUBLICATIONS

Goldenberg et al, "Radioimmunodetection of Prostatic Cancer," J. Amer Med Assoc., 1983, 280, 630-635.

Goldenberg et al, "Carcinoembryonic Antigen Radioimmunodetection in the Evaluation of Colorectal Cancer and in the Detection of Occult Neoplasms," Gastroenterol 1983, 84, 524-532.

Siccardi et al, "Multicenter Study of Immunoscintigraphy with Radiolabeled Monoclonal Antibodies in Patients with Melanoma," Cancer Res 1986, 46, 4817-4822.

Epenetos et al, "1 Radioiodinated Antiboay Imaging of Occult Ovarian Cancer," Cancer 1985, 55, 984-987.

Philben et al, "The Effect of Tumor CEA Content and Tumor Size on Tissue Uptake of Indium 111-Labeled Anti-CEA Monoclonal Antibody," Cancer 1986, 57, 571-576.

Chiou et al, "Dynamic Interaction of Indium-Labeled Monoclonal Antibodies With Surface Antigens of Solid Tumors Visualized in Vivo by External Scintigraphy," Cancer Inst. 1986, 76, 849-855.

Colcher et al, "Radiolocalization of Human Mammary Tumors in Athymic Mice by a Monoclonal Antibody," Cancer Res 1983, 43, 736-742.

Keenan A.M. et al, "Radioimmunoscintigraphy of Human Colon cancer Xenografts in Mice with Radioiodinated Monoclonal Antibody 872.3," J Nucl Med 1984, 25, 1197-1203.

Colcher D. et al, "Quantitative Analyses of Selective Radiolabeled Monoclonal Antibody Localization in Metastatic Lesions of Colorectal Cancer Patients," Cancer Res., 1987, 47, 11851189.

Estaban, J.M. et al "Quantitative and Qualitative Aspects of Radiolocalization in Colon Cancer Patients of Intravenously Administered MAb B72.3," Intl J. Cancer 1987, 39, 50-59.

Martin D.T. et al, "successful Experimental Use of a Self-Contained Gamma Detecting Device," 1984, Curr Surg. 41, 193-194.

Martin E.W. Jr., et al, "Radioimmunoguided Surgery: Intraoperative Use of Monoclonal Antibody 17-1A in Colorectal Cancer," Hybridoma 1986, 5, S97-S108.

Martin D.T, et al, "Intraoperative Radioimmunodetection of Colorectal Tumor With a Hand-Held Radiation Detector," Am J. Surg 1985, 150, 672-675.

Meares et al, "Conjugation of Antibodies with Bifunctional Chelating Agents: Isothiocyanate and Bromoacetamide Reagents, Methods of Analysis, and Subsequent Addition of Metal Ions," Anal Biochem, 142, 1984, 68-78.

Krejcarek et al, "Covalent Attachment of Chelating Groups to Macromolecules," Biochem and Biophys. Res. Comm 1977, 77, 581-585.

Radosevic et al, "Colony lift assay using cell-coated filters: a fast and efficient method to screen phage libraries for cell-binding clones," J. Immunol Meth 2003, 272: 219-233.

English Language Translation of Abstract; KR Publication No. KR100162021, Published Aug. 27, 1998; Applicant: Korea Institute of Science and Technology; Application Filing Date: Jul. 27, 1995; Title: Method for Producing Erythropoietin; (2 pgs.).

Gonzales, Noreen R. et al.; "Minimizing immunogenicity of the SDR-grafted humanized anitibody CC49 by genetic manipulation of the framework residues"; Molecular Immunology (Oct. 1, 2003); vol. 40, No. 6, pp. 337-349.

Yoon, Sun Ok, et al.; "Construction, Affinity Maturation, and Biological Characterization of an Anti-tumor-associated Glycoprotein 72 Humanized Antibody"; Journal of Biological Chemistry (Mar. 17, 2006); vol. 281, No. 11, pp. 6985-6992.

Lim, S.J., et al.; "Affinity Enhanced Humanized Anit-Tag-72 Antibody (3E8) Using Phage Displayed Library Technology for Radioimmunotherapy"; Journal of Nuclear Medicine (May 1, 2002); vol. 43, No. 5, pp. 269P.

English Translation of pp. 41-42; Kasai, Nobuhiko, et al.; "Nyumonmenekigaku" (1989) vol. 1, (1 pg.).

Kasai, Nobuhiko, et al.; "Nyumonmenekigaku" (1989) vol. 1, pp. 41-42.

Database EMBL [Online] (Feb. 21, 2008); retrieved from EBI accession No. DI532963; Database accession No. DI532963; (1 pg.).

Hofman et al, "Stability of T- and B-cell Numbers in Human Peripheral Blood," Am J. Clin Pathol, 1982, 77(6): 710-713.

Schier R. et al, "Isolation of picomolar affinity anti-c-erbB2 single-chain Fv by molecular evolution of the complementary determining regions in the center of the antibody binding sit" J Mol Biol. Nov. 8, 1996 vol. 263(4) pp. 551-567.

Jackson Jr et al, "In vitro antibody maturation. Improvement of a high affinity, neutralizing antibody against IL-1 beta" J Immunol, Apr. 1, 1995, vol. 154(7) pp. 3310-3319.

Casali P et al, "Structure and function of natural antibodies" Curr Top Microbiol Immunol, 1996, vol. 210, pp. 167-179.

* cited by examiner

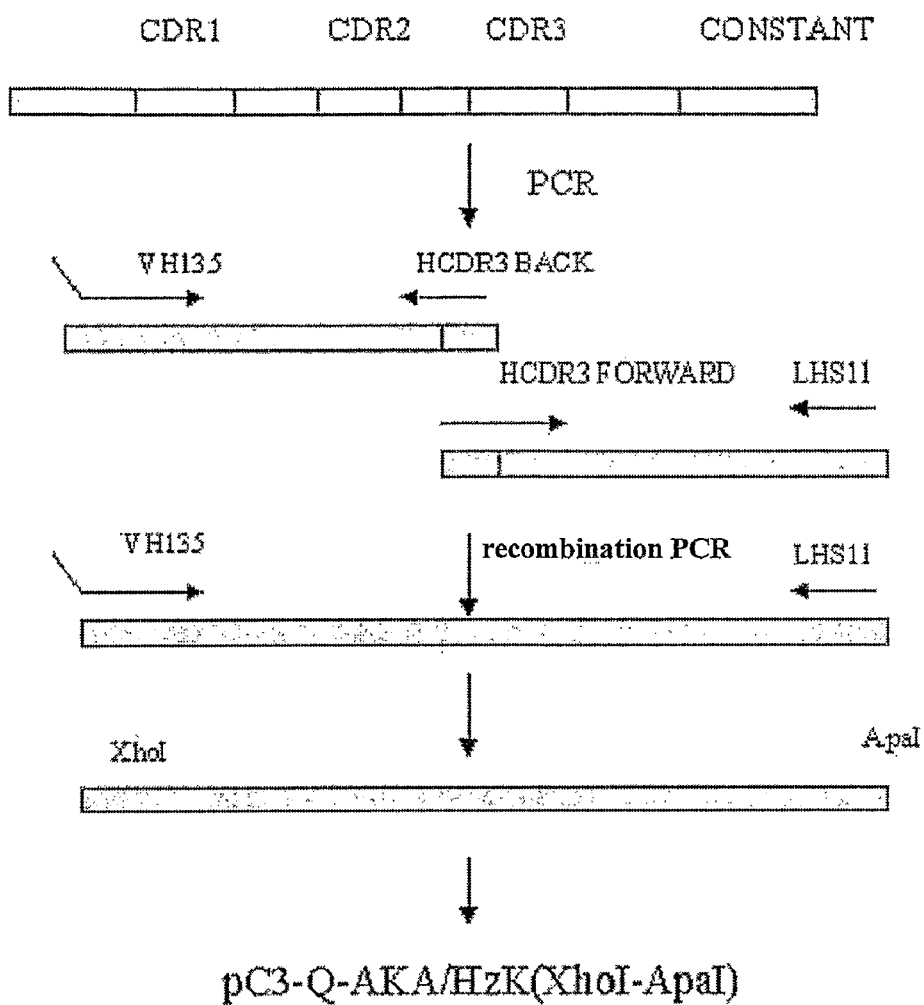

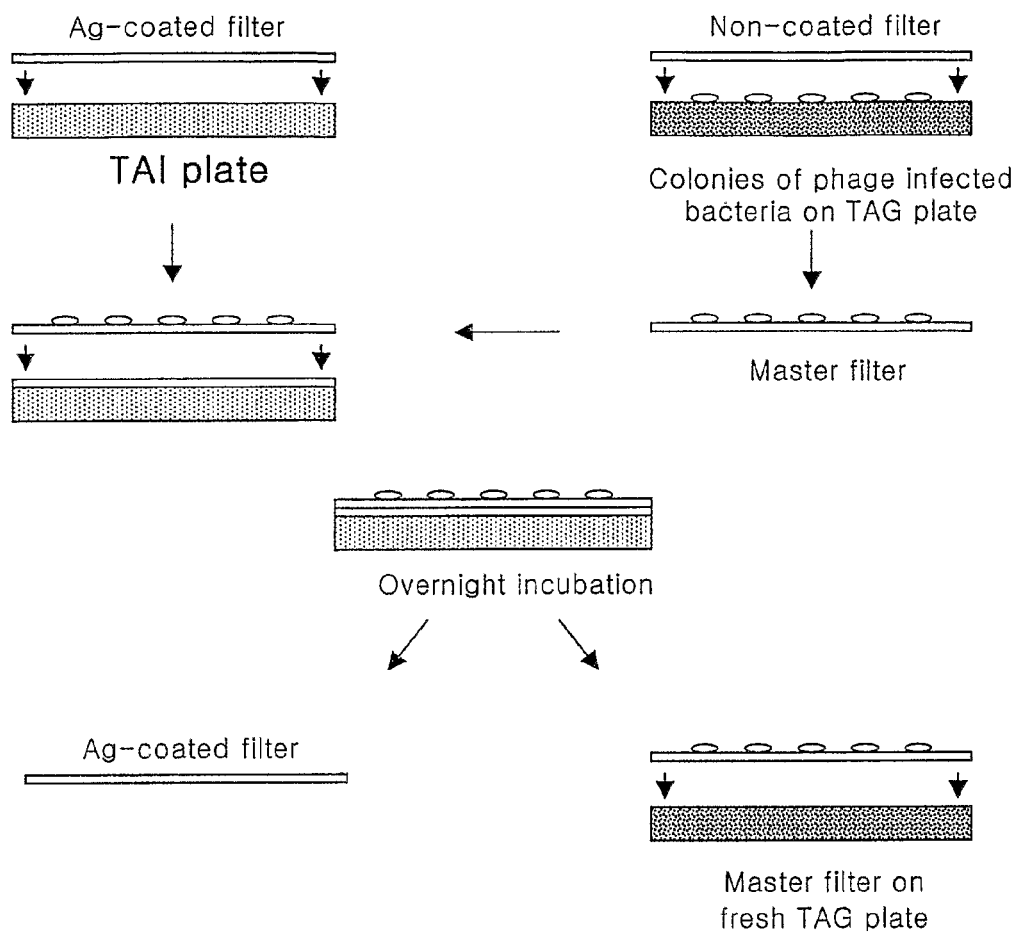
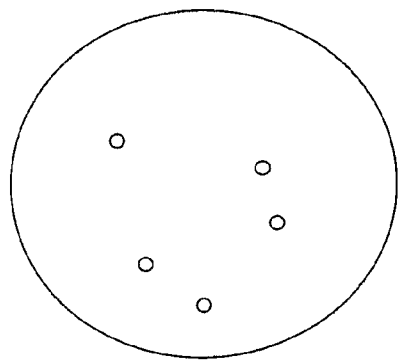
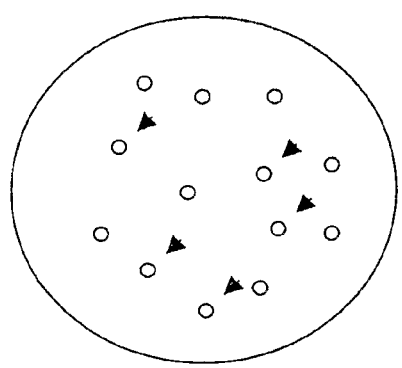

3

|  |  | FR1 | CDR1 |
|---|---|---|---|
| Seq. ID No. 1 | AKA | QVQLVQSGAEVKKPGASVKVSCKASGYTFT | DHAIH |
| Seq. ID No. 2 | 3C4 | QVQLVQSGAEVKKPGASVKVSCKASGYTFT | DHAIH |
| Seq. ID No. 3 | 3D5 | QVQLVQSGAEVKKPGASVKVSCKASGYTFT | DHAIH |
| Seq. ID No. 4 | 3E8 | QVQLVQSGAEVKKPGASVKVSCKASGYTFT | DHAIH |
| Seq. ID No. 5 | NV | QVQLVQSGAEVKKPGASVKVSCKASGYTFT | DHAIH |
| Seq. ID No. 6 | NI | QVQLVQSGAEVKKPGASVKVSCKASGYTFT | DHAIH |

|  |  | FR2 | CDR2 |
|---|---|---|---|
| Seq. ID No. 1 | AKA | WVRQAPGQRLEWMG | YFSPGNDDFKYSQKFQG |
| Seq. ID No. 2 | 3C4 | WVRQAPGQRLEWMG | YFSPGNDDFKYSQKFQG |
| Seq. ID No. 3 | 3D5 | WVRQAPGQRLEWMG | YFSPGNDDFKYSQKFQG |
| Seq. ID No. 4 | 3E8 | WVRQAPGQRLEWMG | YFSPGNDDFKYSQKFQG |
| Seq. ID No. 5 | NV | WVRQAPGQRLEWMG | YFSPGNDDFKYSQKFQG |
| Seq. ID No. 6 | NI | WVRQAPGQRLEWMG | YFSPGNDDFKYSQKFQG |

|  |  | FR3 | CDR3 | FR4 |
|---|---|---|---|---|
| Seq. ID No. 1 | AKA | RVTITADKSASTAYMELSSLRSEDTAVYYCAR | SLNMAY | WGQGTLVTVSS |
| Seq. ID No. 2 | 3C4 | RVTITADKSASTAYMELSSLRSEDTAVYYCAR | SLVQGY | WGQGTLVTVSS |
| Seq. ID No. 3 | 3D5 | RVTITADKSASTAYMELSSLRSEDTAVYYCAR | SLIQGY | WGQGTLVTVSS |
| Seq. ID No. 4 | 3E8 | RVTITADKSASTAYMELSSLRSEDTAVYYCAR | SWIMQY | WGQGTLVTVSS |
| Seq. ID No. 5 | NV | RVTITADKSASTAYMELSSLRSEDTAVYYCAR | SLVMAY | WGQGTLVTVSS |
| Seq. ID No. 6 | NI | RVTITADKSASTAYMELSSLRSEDTAVYYCAR | SLIMAY | WGQGTLVTVSS |

4
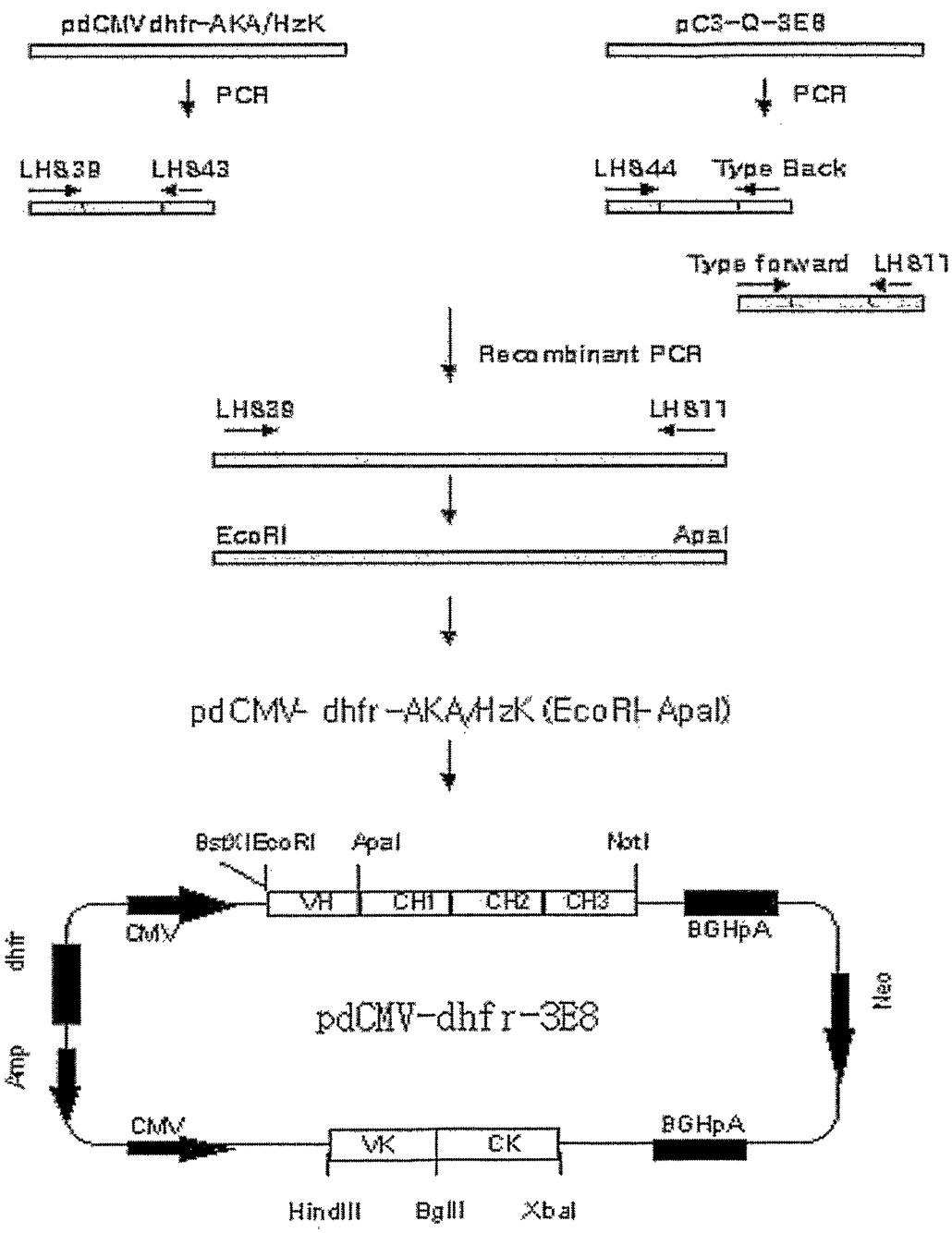

5a
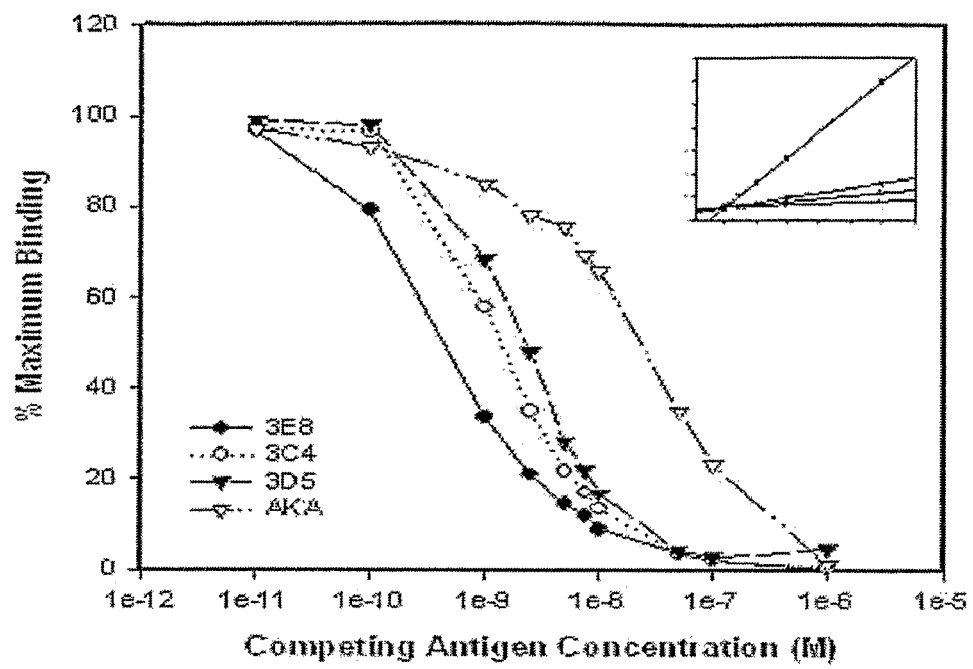
5b
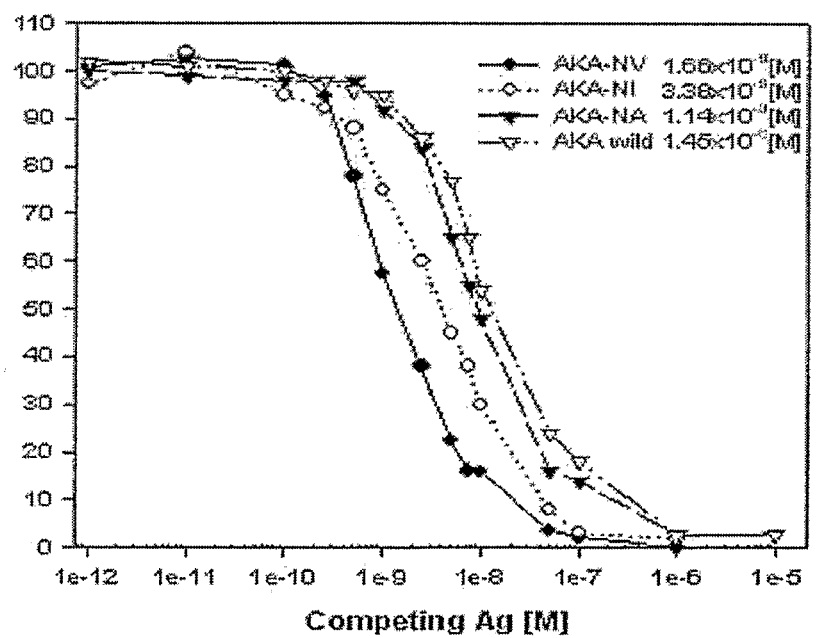

6

|   | 1 | 2 |
|---|---|---|
| 175 |   |   |
| 83 |   |   |
| 62 |   |   |
| 47.5 |   |   |
| 32.5 |   |   |
| 25 |   |   |

7

|  |  | FR1 | CDR1 |
|---|---|---|---|
| Seq. ID No. 21 | HzK | DIVMTQSPDSLAVSLGERATINC | KSSQSVLYSSNNKNYLA |
|  | BSM22 | ...................H. | .....I............ |

|  |  | FR2 | CDR2 |
|---|---|---|---|
| Seq. ID No. 21 | HzK | WYQQKPGQPPKLLIY | WASTRES |
|  | BSM22 | .............L. | ......A |

|  |  | FR3 |
|---|---|---|
| Seq. ID No. 21 | HzK | GVPDRFSGSGSGTDFTLTISSLQAEDVAVYYC |
|  | BSM22 | ........G................P..S.T... |

|  |  | CDR3 | FR4 |
|---|---|---|---|
| Seq. ID No. 21 | HzK | QQYYSYPLT | FGGGTKVEIK |
|  | BSM22 | ...NT.... | .......... |

8
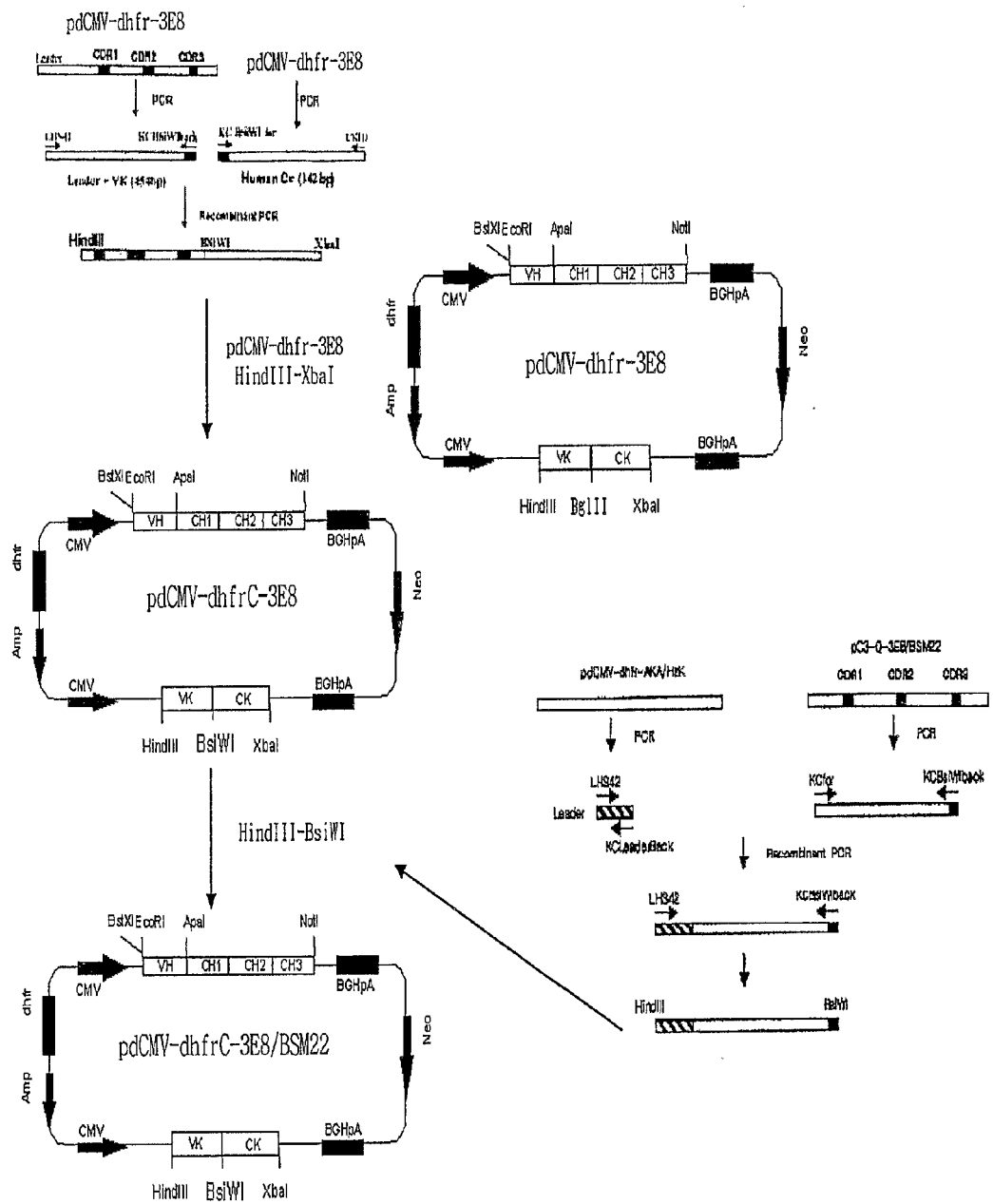

9
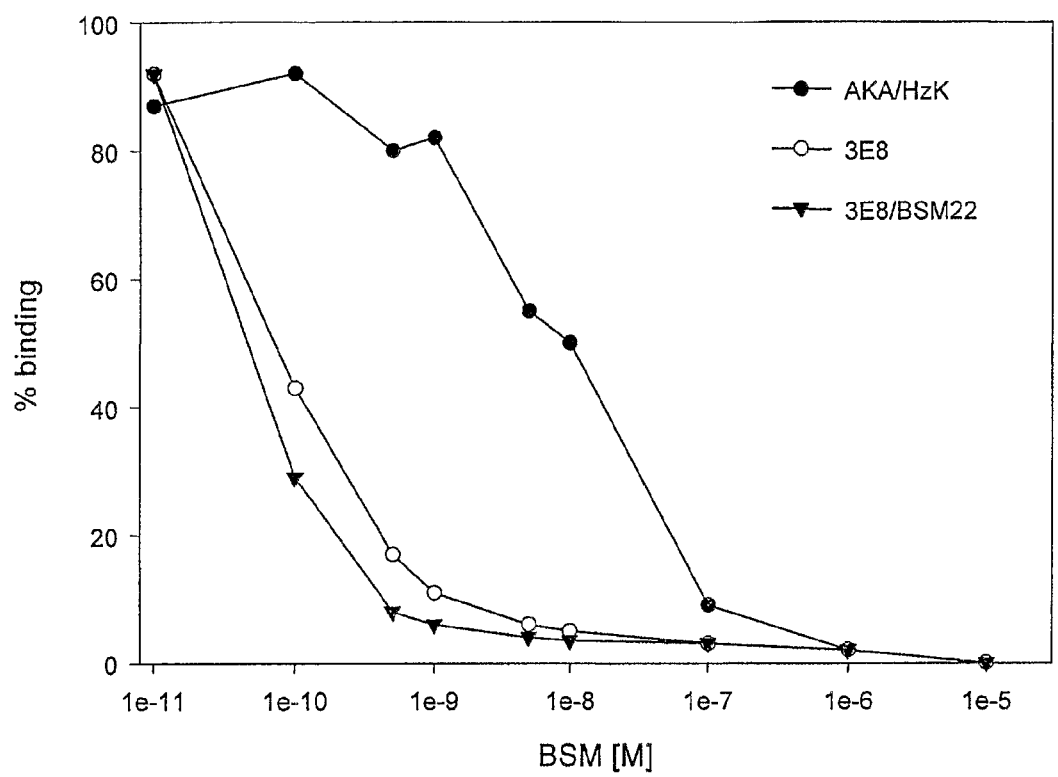

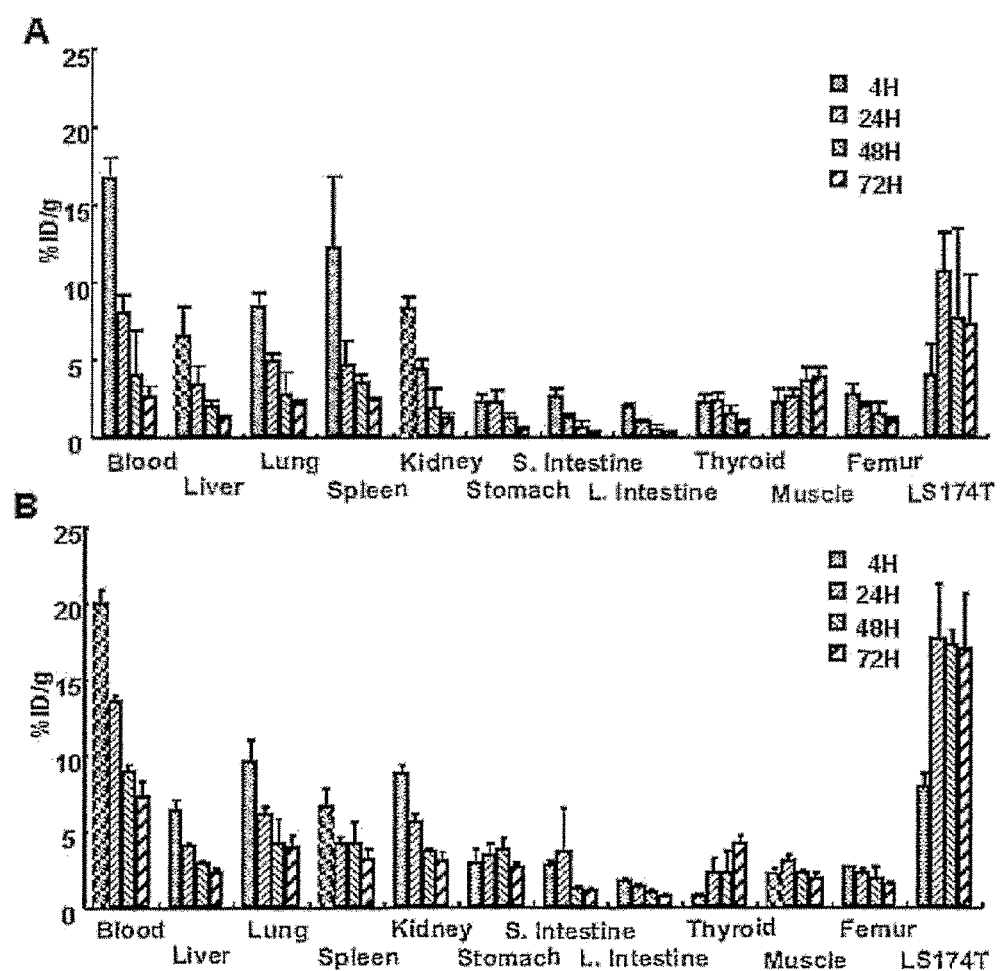

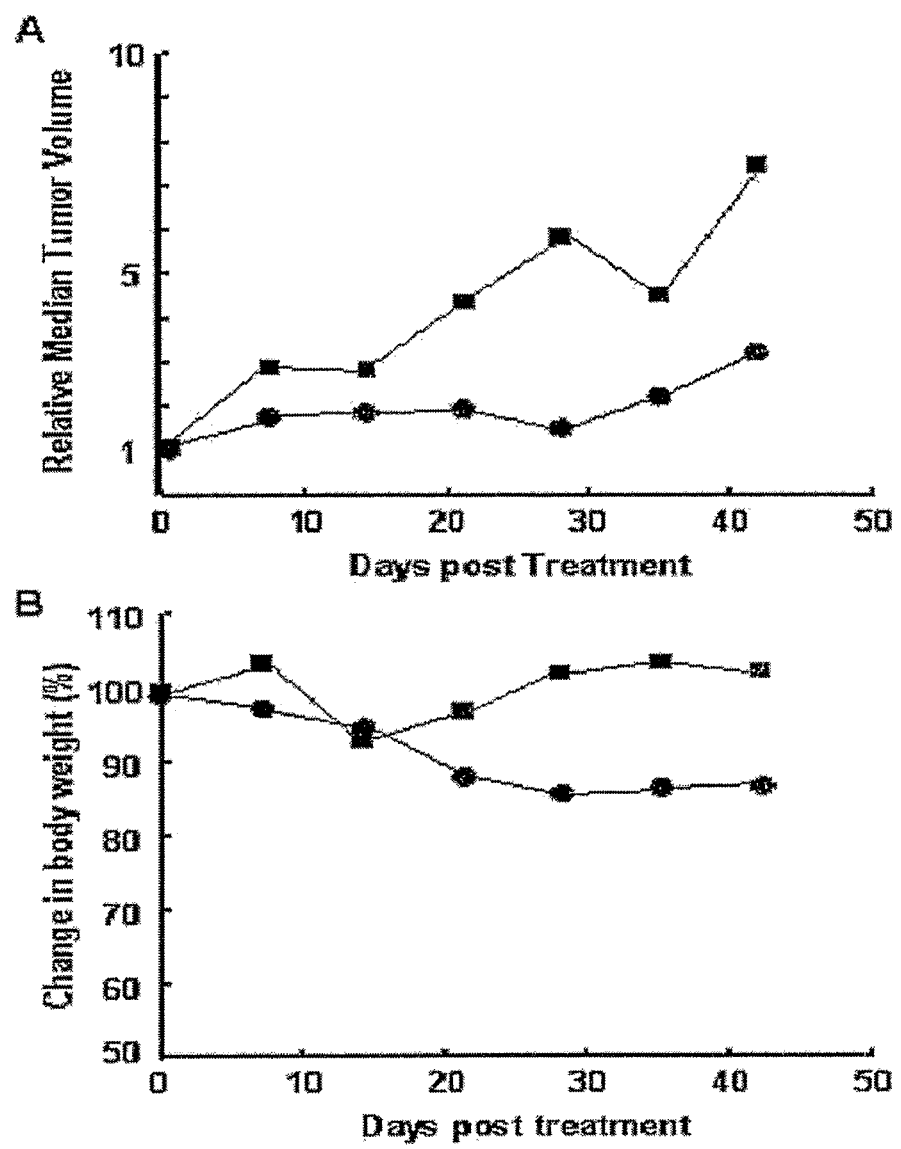

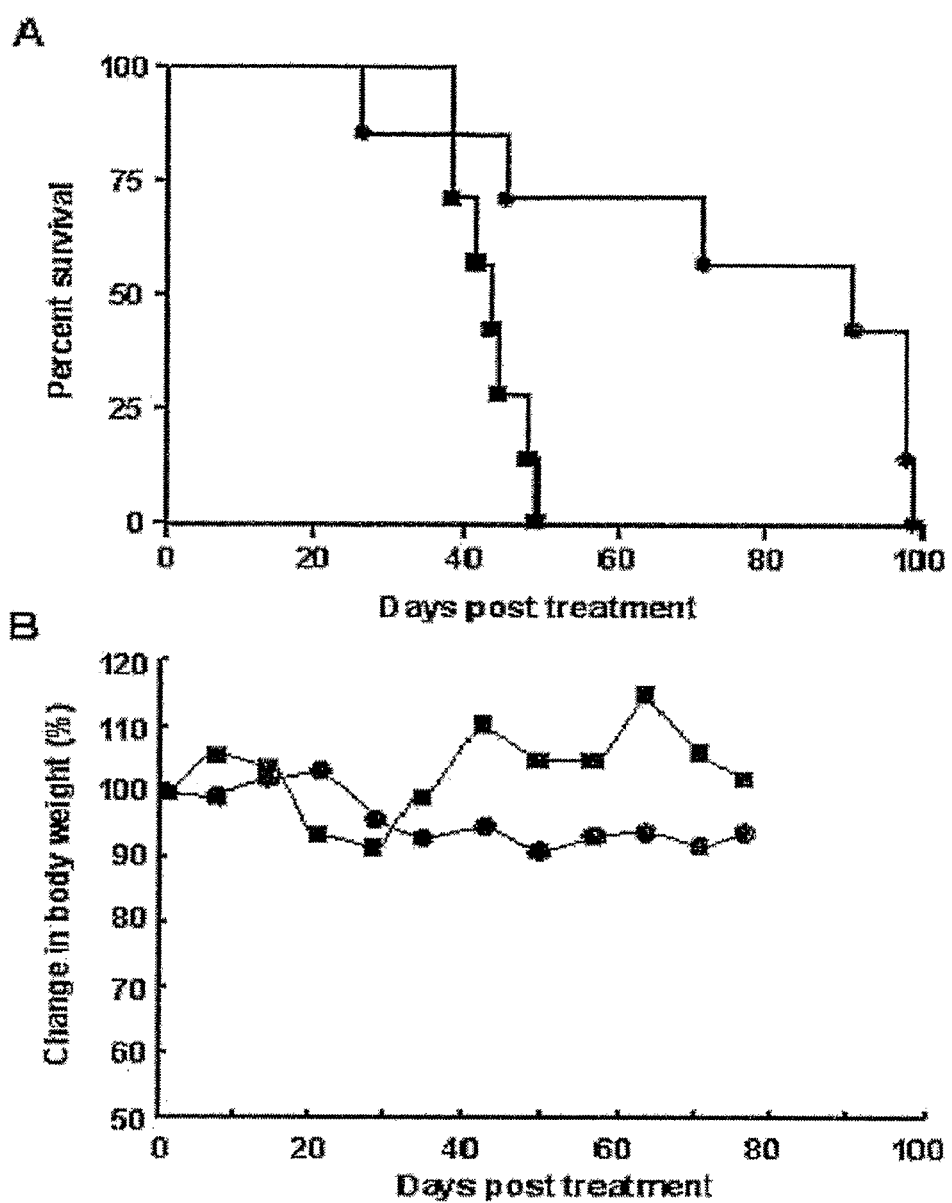

HUMANIZED ANTI-TAG-72 MONOCLONAL ANTIBODIES

TECHNICAL FIELD

The present invention relates to humanized antibodies specific to a tumor-associated glycoprotein-72 (TAG-72), and anticancer compositions comprising the humanized antibodies.

BACKGROUND ART

Tumor-associated glycoprotein-72 (hereinafter, referred to simply as "TAG-72") is a mucin protein, which is a tumor-associated antigen expressed in a broad range of human carcinomas, including colon cancer, stomach cancer, pancreatic cancer, breast cancer and ovarian cancer. A murine monoclonal antibody B72.3 is the first antibody specific to TAG-72, which was developed using a membrane fraction of human breast cancer tissue as an immunogen by Dr. Jeffrey Schlom's group in NIH National Cancer Institute in the early 1980's (Colcher et al., 1981, Proc. Natl. Acad. Sci. USA, 78(5):3199-3203). Thereafter, second-generation antibodies having higher antigen binding affinity than B72.3, such as CC49 and CC83, were developed by the same research group (Muraro et al., 1988, Cancer Res., 48(16):4588-4596).

CC49 or CC83 was found to bind to more than 80% of colon cancer and about 50% of breast cancer, but rarely binds to normal tissues. Also, in vivo imaging using $^{131}$I-labeled CC49 or CC83 in cancer patients resulted in the detection of primary cancer and metastasized cancer (Divgi et al., 1994, Nucl. Med. Biol., 21(1):9-15). However, the repeated administration of the murine monoclonal antibodies to the body caused side effects or reduced therapeutic efficacy by inducing immune responses in the body. In order to minimize these undesired immune responses, humanized antibodies have been constructed by grafting complementarity determining regions (CDR) and some amino acid residues of a framework region (FR) of murine antibodies onto human antibody (Owens et al, 1994, J. Immunol. Methods, 168(2):149-65). These humanized antibodies were reported to greatly reduce undesired immune responses in patients when repeatedly administered to patients (Brown et al., 1991, Proc. Natl. Acad. Sci. USA, 88:2663).

In one study involving humanized antibodies against the TAG-72 antigen, a humanized antibody (HuCC49) of murine monoclonal antibody CC49 was developed by grafting CDRs of the murine monoclonal antibody CC49 onto light and heavy chain FRs of human monoclonal antibodies, while retaining those murine framework residues that are required for the preservation of the antigen combining-site structure (Kashmiri et al., Hybridoma 14:461-473, 1995).

U.S. Pat. No. 5,976,531 describes a Hum4$V_L$, $V_H$ antibody specific to TAG-72, which consists of a light chain variable region ($V_L$), which is encoded by DNA derived from a human kappa subgroup IV germline gene (Hum4 $V_L$), and a heavy chain variable region ($V_H$) capable of combining with the $V_L$ to form a three dimensional structure having the ability to specifically bind to TAG-72.

U.S. Pat. No. 6,495,137 discloses a humanized anti-TAG-72 antibody or a fragment thereof, which comprises a CDR-grafted light chain having light chain CDRs of a murine anti-TAG-72 antibody grafted onto Hum4$V_L$, wherein the murine anti-TAG-72 antibody is selected from among CC49, CC83, CC46, CC92, CC30 and CC11.

Other various humanized antibodies against TAG-72 were developed. However, there is a need to develop humanized anti-TAG-72 antibodies that have high antigen binding capacity and a reduced risk of inducing immune responses in humans.

In this regard, the present inventors, as described in Korean Pat. No. 0318761 submitted by the present inventors, identified human genes having sequences most similar to CDR and FR sequences of a murine anti-TAG-72 antibody, prepared light chain and heavy chain genes of a humanized antibody using the identified human genes, cloning the obtained genes into an expression vector, transforming a host cell with the expression vector, and cultivating the host cell, thereby developing a humanized anti-TAG-72 antibody, AKA/HzK. Compared to the humanized antibody HuCC49, the humanized antibody AKA/HzK has CDRs and FRs in which amino acid residues are replaced by amino acids more similar to those in humans and thus has reduced immunogenicity in humans, while substantially retaining antigen binding ability almost similar to that of the HuCC49 antibody. Despite this development, there is still the need for functionally excellent antibodies having a reduced risk of inducing immune responses in humans and improved antigen binding ability and affinity.

Based on this background, the present inventors, in order to prepare an antibody having excellent binding ability and affinity to TAG-72, prepared humanized heavy chain library by random mutagenesis of the CDR3 of heavy chain variable region of the humanized antibody AKA/HzK, and performed a colony lift assay using the library-expressing cells to select mutant Fab clones having high antigen binding ability. The selected clones were assessed for their antigen binding ability by competitive ELISA. As a result, a novel antibody having enhanced antigen binding ability and antigen binding affinity to TAG-72 was constructed. Further, the present inventors constructed a humanized antibody by replacing a light chain of the novel humanized antibody with a human light chain, thereby leading to the present invention.

DISCLOSURE OF THE INVENTION

It is therefore an object of the present invention to provide a humanized antibody against tumor-associated glycoprotein-72 (TAG-72), which comprises (i) a heavy chain variable region having an amino acid sequence of SEQ ID No. 1, in which one or more of 100th to 103rd amino acid residues are replaced with another amino acid, and (ii) a light chain variable region having an amino acid sequence represented by SEQ ID No. 21 or 22.

It is another object of the present invention to provide nucleic acid sequences encoding the heavy chain variable region and the light chain variable region.

It is a further object of the present invention to provide a recombinant vector comprising the nucleic acid sequence encoding the heavy chain variable region and the nucleic acid sequence encoding the light chain variable region.

It is yet another object of the present invention to provide a transformant transformed with the recombinant vectors.

It is still another object of the present invention to provide a method of preparing the humanized antibody by culturing the transformant.

It is still another object of the present invention to provide an anticancer composition comprising the humanized antibody.

It is still another object of the present invention to provide a method of treating or preventing cancer by administering the humanized antibody.

It is still another object of the present invention to provide a method of diagnosing cancer by administering the humanized antibody.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a schematic presentation of a process for constructing an expression vector of a mutated antibody by randomly mutating amino acid residues at positions 99 to 103 of an amino acid sequence encoding the heavy chain HCDR3 of a humanized antibody AKA/HzK against a tumor-associated glycoprotein TAG-72, which is represented by SEQ ID No. 1;

FIG. 2 is a schematic presentation of a colony lift assay for selecting mutant Fab clones having high antigen binding affinity;

FIG. 3 shows amino acid sequences of heavy chain variable regions of mutant clones having high antigen binding affinity;

FIG. 4 is a schematic representation of a process for constructing a plasmid for expression of a 3E8 mutant having the highest antigen binding affinity in whole IgG form;

FIGS. 5a and 5b are graphs in which 3E8, 3C4, 3D5, NV and NI antibodies in IgG form are compared for antigen binding capacity with a conventional antibody AKA/Hzk in IgG form;

FIG. 6 is a gel photograph of the electrophoretic separation of an antibody of the present invention under reduction and non-reduction conditions, wherein molecular weights of the antibody and its subunits are determined (lane 1: reduction condition; lane 2: non-reduction condition)

FIG. 7 is an amino acid sequence alignment of a human light chain variable region of a 3E8/BSM22 antibody and a light chain variable region of a conventional antibody AKA/HzK;

FIG. 8 is a schematic representation of a process for constructing a plasmid for expression of a 3E8/BSM22 antibody in whole IgG form;

FIG. 9 is a graph in which the antigen binding affinity of 3E8 and 3E8/BSM22 antibodies is compared with that of AKA/HzK (○: 3E8; ▼: 3E8/BSM22; ●: AKA/HzK);

FIG. 10 graphically shows the in vivo distribution and tumor targeting ability of AKA/HzK and 3E8 antibodies, wherein $^{125}$I-AKA/HzK (A panel) and $^{125}$I-3E8 (B panel) were intravenously injected into an athymic mouse xenograft model of human colon cancer and their biodistribution and tumor targeting were assessed in the mice;

FIG. 11 graphically shows the radioimmunotherapeutic efficacy of a 3E8 antibody, which is determined by measuring the inhibitory effect of the 3E8 antibody on tumor growth, wherein the tumor doubling time (Td; A panel) and changes in body weight (B panel) were estimated in mice administered with $^{131}$I-3E8 (●) and 3E8 (■); and FIG. 12 graphically shows the radioimmunotherapeutic efficacy of a 3E8 antibody, which is determined by measuring mouse survival rates, wherein the survival rates (A panel) and changes in body weight (B panel) were estimated in mice administered with $^{131}$I-3E8 (●) and 3E8 (■).

BEST MODE FOR CARRYING OUT THE INVENTION

In one aspect, the present invention relates to a humanized antibody against tumor-associated glycoprotein-72 (TAG-72), which comprises (i) a heavy chain variable region having an amino acid sequence of SEQ ID No. 1, in which 100th to 103rd amino acid residues have a sequence represented by Sequence Formula 1, below, and (ii) a light chain variable region having an amino acid sequence represented by SEQ ID No. 21 or 22.

-X100-X101-X102-X103-(SEQ ID NO:35)   [Sequence Formula 1]

wherein, X100 is an amino acid residue that is leucine (Leu) or tryptophan (Trp), X101 is an amino acid residue that is isoleucine (Ile), valine (Val), leucine (Leu) or alanine (Ala), X102 is an amino acid residue that is methionine (Met) or glutamine (Gln), and X103 is an amino acid residue that is alanine (Ala), glutamine (Gln) or glycine (Gly).

Mouse-derived antibodies induce undesired immune responses in humans because they are recognized as antigens in humans, and new human anti-mouse antibodies (HAMAs) against the mouse antibodies are produced, thereby inducing undesired immune responses. Many attempts have been made to overcome this problem by reducing the immunogenicity of non-human antibodies in humans. The so-called humanization techniques typically employ a recombinant DNA technique that manipulates a DNA sequence encoding a polypeptide chain of an antibody molecule. The initial preparation method of humanized antibodies is based on creating a chimeric antibody in which a constant region of human antibodies is fused to an antigen binding domain of a non-human antibody. International Pat. Publication No. WO86/01533 discloses a method of preparing a chimeric antibody, which is humanized by linking only a variable region derived from murine antibodies to a human antibody constant region. This chimeric antibody had advantages of displaying lower immune responses than murine antibodies and having improved functions. However, since chimeric antibodies still contain mouse variable regions, that is, amino acid sequences of non-human variable regions, they cause HAMA responses when repeatedly administered to humans.

In order to further humanize chimeric antibodies, many attempts have been made to recombine CDRs of murine monoclonal antibodies displaying antigen binding capacity with FRs of human antibodies, based on the concept that the recombination does not induce immune responses in humans while retaining antigen binding specificity and affinity of the murine antibodies (Jones et al., 1986, Nature, 4; 321(6069): 522-525). Humanized antibodies prepared by CDR grafting, which is based on grafting CDR loops of murine antibodies onto human antibodies, contain much fewer non-human amino acid sequences and thus have a reduced risk of HAMA responses compared to chimeric antibodies, but may have lower antigen binding affinity. FRs of parent murine antibodies may be required for allowing humanized antibodies to retain the ability of their parent antibodies to bind to their antigens. In this regard, when several amino acid residues of FRs considered to affect the CDR structure were replaced with those of murine antibody, the antigen binding affinity of a humanized antibody was enhanced to levels similar to that of a parent murine antibody (Riechmann et al., 1988, Nature, 332: 323-327; Queen et al., 1999, Proc. Natl. Acad. Sci. USA, 86: 10023-10029; Tempest et al., 1991, Biol. Technology, 9:266-271; Co et al., 1991, Nature, 351:501-502).

The term "humanized antibody", as used herein, as described above, generally means an antibody that is non-immunogenic or has reduced immunogenicity in humans. A humanized antibody is an antibody having an altered amino acid sequence, and the amino acid sequence of the antibody may be reconstituted according to intended purposes. A large number of changes are possible, which range from changes of one or several amino acids to complete reconstitution of variable and/or constant regions of an antibody. Typically, variations of variable regions are performed to enhance binding capacity and affinity to an antigen, and variations in constant regions are performed to improve effector functions, such as complement fixation, and antibody-dependent cell-mediated cytotoxicity.

The humanized antibody of the present invention is an antibody that is obtained by mutating the CDR3 of a heavy chain variable region of a humanized antibody, AKA/HzK, which is constructed by the present inventors prior to the present. The humanized antibody of the present invention has improved antigen binding capacity and affinity compared to the AKA/HzK, which has a heavy chain variable region having an amino acid sequence represented by SEQ ID No. 1 and a light chain variable region having an amino acid sequence represented by SEQ ID No. 21.

The term "variable region", as used herein, means a portion of an antibody molecule, which functions to specifically bind to an antigen and shows many variations in sequence. Three complementarity determining regions, CDR1, CDR2 and CDR3, are present in a variable region. "Complementarity determining regions (CDRs)" are loop-like regions that participate in antigen recognition, and the specificity of an antibody for an antigen is determined according to changes in sequences of CDRs. In detail, in the present invention, an antibody with improved antigen binding affinity was constructed by a variation in an amino acid sequence of CDR3. "Framework regions (FRs)", interposed between CDRs in an appropriate orientation, serve to hold the CDR loops, and include FR1, FR2, FR3 and FR4. The antibody heavy chain variable region of the present invention is composed of an FR1 spanning positions 1 to 30, a CDR1 spanning positions 31 to 35, an FR2 spanning positions 36 to 49, a CDR2 spanning positions 50 to 66, an FR3 spanning positions 67 to 98, a CDR3 spanning positions 99 to 104, and an FR4 spanning positions 105 to 115. The antibody light chain variable region of the present invention is composed of an FR1 spanning positions 1 to 23, a CDR1 spanning positions 24 to 40, an FR2 spanning positions 41 to 55, a CDR2 spanning positions 56 to 62, an FR3 spanning positions 63 to 94, a CDR3 spanning positions 95 to 103, and an FR4 spanning positions 104 to 113.

The present inventors found that when the asparagine (Asn) residue at position 101 (Kabat No: 97) of the CDR3 of a heavy chain variable region having the amino acid sequence of SEQ ID No. 1 is replaced with an aliphatic residue, the humanized antibody has enhanced affinity for TAG-72. In the present invention, the aliphatic residue means isoleucine, valine, leucine or alanine.

In a detailed aspect, the present invention provides a humanized antibody against TAG-72, comprising (i) a heavy chain variable region having the amino acid sequence of SEQ ID No. 1, in which an asparagine residue at position 101 (Kabat No: 97) is replaced with an aliphatic residue, for example, isoleucine, valine, leucine or alanine, and a leucine residue at position 100 (Kabat No: 96) is replaced with a tryptophan residue, and/or a methionine residue at position 102 (Kabat No: 98) is replaced with a glutamine residue, and/or an alanine residue at position 103 (Kabat No: 99) is replaced with a glutamine or glycine residue, and (ii) a light chain variable region having an amino acid sequence represented by SEQ ID No. 21.

More preferably, in the heavy chain variable region, the asparagine residue at position 101 is replaced with valine, the methionine residue at position 102 with glutamine, and the alanine residue at position 103 with glycine. Thus, there is provided a humanized anti-TAG-72 antibody, 3C4, which comprises a heavy chain variable region having an amino acid sequence represented by SEQ ID No. 2 and a light chain variable region having an amino acid sequence represented by SEQ ID No. 21. Also, more preferably, in the heavy chain variable region, the asparagine residue at position 101 is replaced with isoleucine, the methionine residue at position 102 with glutamine, and the alanine residue at position 103 with glycine. Thus, there is provided a humanized anti-TAG-72 antibody, 3D5, which comprises a heavy chain variable region having an amino acid sequence represented by SEQ ID No. 3 and a light chain variable region having an amino acid sequence represented by SEQ ID No. 21. Also, more preferably, in the heavy chain variable region, the asparagine residue at position 101 is replaced with isoleucine, the leucine residue at position 100 with tryptophan, and the alanine residue at position 103 with glutamine. Thus, there is provided a humanized anti-TAG-72 antibody, 3E8, which comprises a heavy chain variable region having an amino acid sequence represented by SEQ ID No. 4 and a light chain variable region having an amino acid sequence represented by SEQ ID No. 21. Also, more preferably, in the heavy chain variable region, the asparagine residue at position 101 is replaced with valine. Thus, there is provided a humanized anti-TAG-72 antibody, NV, which comprises a heavy chain variable region having an amino acid sequence represented by SEQ ID No. 5 and a light chain variable region having an amino acid sequence represented by SEQ ID No. 21. Also, more preferably, in the heavy chain variable region, the asparagine residue at position 101 is replaced with isoleucine. Thus, there is provided a humanized anti-TAG-72 antibody, NI, which comprises a heavy chain variable region having an amino acid sequence represented by SEQ ID No. 6 and a light chain variable region having an amino acid sequence represented by SEQ ID No. 21.

The aforementioned antibodies have largely enhanced affinity compared to the conventional antibody AKA/HzK. The whole antibody 3C4 has an antigen binding affinity ($K_D$) of $1.33 \times 10^{-9}$ M, the whole antibody 3D5 has a $K_D$ of $2.27 \times 10^{-9}$ M, and the whole antibody 3E8 has a $K_D$ of $0.65 \times 10^{-9}$ M. These $K_D$ values are respectively about 11, 6 and 22-fold higher than the $K_D$ value of $1.45 \times 10^{-8}$ M of AKA/HzK. The whole NV antibody has a $K_D$ of $1.66 \times 10^{-9}$ M, and the whole NI antibody has a $K_D$ of $3.38 \times 10^{-9}$ M. These $K_D$ values are respectively about 8 and 4-fold higher than the $K_D$ value of $1.45 \times 10^{-8}$ M of AKA/HzK.

The present inventors intended to replace a light chain of the antibodies with a human light chain.

In order to select a human light chain that can be used along with a heavy chain variable region of the humanized antibodies by replacing a humanized light chain, a human light chain library was prepared from human peripheral blood lymphocytes (PBL). Human light chain DNA fragments were inserted into an expression vector of Fab of a humanized antibody 3E8 showing the best effect, pC3-Q-3E8, instead of a humanized light chain gene, and a colony lift assay was performed to select mutant clones having strong antigen binding capacity. Cell clones having better antigen binding capacity than the wild-type 3E8 Fab were isolated, and their light chain variable regions were subjected to DNA sequencing. The DNA sequencing revealed that a clone has a light chain variable region having an amino acid sequence represented by SEQ ID No. 22. The human light chain variable region having an amino acid sequence represented by SEQ ID No. 22, obtained in this way, is capable of replacing a light chain variable region of the humanized antibodies by a commonly used recombinant DNA technique.

In another detailed aspect, the present invention provides a humanized antibody against TAG-72, comprising (i) a heavy chain variable region having an amino acid sequence of SEQ ID No. 1, in which an asparagine residue at position 101 (Kabat No: 97) is replaced with an aliphatic residue, for example, isoleucine, valine, leucine or alanine, and a leucine residue at position 100 (Kabat No: 96) is replaced with a tryptophan residue, and/or a methionine residue at position 102 (Kabat No: 98) is replaced with a glutamine residue, and/or an alanine residue at position 103 (Kabat No: 99) is replaced with a glutamine or glycine residue, and (ii) a light chain variable region having an amino acid sequence represented by SEQ ID No. 22.

Preferably, there is provided a humanized antibody against TAG-72, comprising a heavy chain variable region having an amino acid sequence represented by SEQ ID No. 2 and a light chain variable region having an amino acid sequence represented by SEQ ID No. 22. Also, preferably, there is provided a humanized antibody against TAG-72, comprising a heavy chain variable region having an amino acid sequence represented by SEQ ID No. 3 and a light chain variable region having an amino acid sequence represented by SEQ ID No. 22. Also, preferably, there is provided a humanized antibody against TAG-72, comprising a heavy chain variable region having an amino acid sequence represented by SEQ ID No. 4 and a light chain variable region having an amino acid sequence represented by SEQ ID No. 22. Also, preferably, there is provided a humanized antibody against TAG-72, comprising a heavy chain variable region having an amino acid sequence represented by SEQ ID No. 5 and a light chain variable region having an amino acid sequence represented by SEQ ID No. 22. Also, preferably, there is provided a humanized antibody against TAG-72, comprising a heavy chain variable region having an amino acid sequence represented by SEQ ID No. 6 and a light chain variable region having an amino acid sequence represented by SEQ ID No. 22.

The above antibodies have largely enhanced affinity compared to the conventional antibody AKA/HzK. Among them, a humanized antibody, 3E8/BSM22, which comprises a heavy chain variable region having an amino acid sequence represented by SEQ ID No. 4 and a light chain variable region having an amino acid sequence represented by SEQ ID No. 22, is most preferable. The whole 3E8/BSM22 antibody has an antigen binding affinity ($K_D$) of $0.45 \times 10^{-9}$M, which is about 1.5-fold higher than $0.65 \times 10^{-9}$M for the 3E8 antibody.

In the present invention, an "antibody" includes a whole antibody form and functional fragments of an antibody molecule. A whole antibody consists of two full-length light chains and two full-length heavy chains, wherein each light chain is linked to a heavy chain via disulfide bonds. The term "functional fragments of an antibody molecule" indicates fragments retaining antigen binding functions, and include Fab, F(ab'), F(ab')2 and Fv. Among the antibody fragments, Fab contains the variable regions of the light chain and the heavy chain, the constant region of the light chain and the first constant region (CH1) of the heavy chain, and has a single antigen binding site. The Fab' fragments differ from the Fab fragments in terms of having the hinge region containing one or more cysteine residues at the C-terminus of the heavy chain CH1 domain. The F(ab')2 fragments are produced as a pair of Fab' fragments by disulfide bonding formed between cysteine residues of the hinge regions of the Fab' fragments. Fv is the minimum antibody fragment that contains only the heavy chain variable region and the light chain variable region. Recombinant techniques for producing the Fv fragments are described in International Pat. Publication Nos. WO88/10649, WO88/106630, WO88/07085, WO88/07086 and WO88/09344. The disulfide-linked Fv (dsFv) comprises the heavy chain variable region and the light chain variable region that are linked to each other by disulfide bonding. The single-chain Fv (scFv) comprises the heavy-chain variable region and the light-chain variable region that are covalently linked to each other by a peptide linker.

These antibody fragments may be obtained using proteolytic enzymes (for example, whole antibodies are digested with papain to produce Fab fragments, and pepsin treatment results in the production of F(ab')2 fragments), and may be preferably prepared by recombinant DNA techniques. In the present invention, an antibody is preferably in a Fab form or a whole antibody form.

The humanized antibodies provided in the present invention may be linked to all types of constant regions by a recombinant DNA technique. There are five distinct types of heavy chains based on differences in the amino acid sequences of their constant regions: gamma ($\gamma$), mu ($\mu$), alpha ($\alpha$), delta ($\delta$) and epsilon ($\epsilon$), and the heavy chains include the following subclasses: gamma 1 ($\gamma$1), gamma 2 ($\gamma$2), gamma 3 ($\gamma$3), gamma 4 ($\gamma$4), alpha 1 ($\alpha$1) and alpha 2 ($\alpha$2). Also, there are two types of light chains based on differences in the amino acid sequences of their constant regions: kappa ($\kappa$) and lambda ($\lambda$) types (Coleman et al., Fundamental Immunology, 2nd Ed., 1989, 55-73). Preferably, the heavy chain constant region is gamma 1 or gamma 3, and most preferably, the gamma 1 isotype. Preferably, the light chain constant region is the kappa type.

The constant regions of the antibodies of the present invention include variants having altered amino acid sequences. Preferably, an immunoglobulin constant region variant is a variant that has improved structural stability, for example, against heat, pH, or the like, or improved solubility, or that has improved biological activities, such as disulfide bond formation, affinity for expression hosts, complement binding, association with Fc receptors and antibody-dependent cell-mediated cytotoxicity, by alteration and modification of amino acid sequences, as long as variant does induce immune responses.

In another aspect, the present invention relates to nucleic acid sequences encoding the heavy chain variable region and the light chain variable region.

The nucleic acid sequence encoding the heavy chain variable region encodes an amino acid sequence of SEQ ID No. 1, in which an asparagine residue at position 101 is replaced with an aliphatic residue, for example, isoleucine, valine, leucine or alanine, and a leucine residue at position 100 is replaced with a tryptophan residue, and/or a methionine residue at position 102 is replaced with a glutamine residue, and/or an alanine residue at position 103 is replaced with a glutamine or glycine residue. Preferably, the nucleic acid sequence encodes an amino acid sequence represented by SEQ ID No. 2, 3, 4, 5 or 6.

More preferably, the nucleic acid sequence encoding an amino acid sequence represented by SEQ ID No. 2 has the nucleotide sequence of SEQ ID No. 16. The nucleic acid sequence encoding an amino acid sequence represented by SEQ ID No. 3 has the nucleotide sequence of SEQ ID No. 17. The nucleic acid sequence encoding an amino acid sequence represented by SEQ ID No. 4 has the nucleotide sequence of SEQ ID No. 18. The nucleic acid sequence encoding an amino acid sequence represented by SEQ ID No. 5 has the nucleotide sequence of SEQ ID No. 19. The nucleic acid sequence encoding an amino acid sequence represented by SEQ ID No. 6 has the nucleotide sequence of SEQ ID No. 20.

The nucleic acid sequence encoding the light chain variable region encodes a light chain variable region represented by SEQ ID No. 22. Preferably, the nucleic acid sequence has the nucleotide sequence of SEQ ID No. 23.

The nucleic acid sequences encoding the antibody variable and constant regions are inserted into a recombinant expression vector and expressed.

In a further aspect, the present invention relates to a recombinant vector comprising the nucleic acid sequence encoding a heavy chain variable region and the nucleic acid sequence encoding a light chain variable region.

A preferred recombinant vector comprises a nucleic acid sequence encoding a heavy chain variable region selected from the group consisting of amino acid sequences represented by SEQ ID Nos. 2 to 6 and a light chain variable region selected from the group consisting of amino acid sequences represented by SEQ ID Nos. 21 and 22. In the detailed practice, there is provided a recombinant vector that is pC3-Q-3C4, pC3-Q-3D5, pC3-Q-3E8, pC3-Q-NV, pC3-Q-NI or pC3-Q-3E8/BSM22. Also, there is provided a recombinant vector that is pdCMV-dhfr-3C4, pdCMV-dhfr-3D5, pdCMV-dhfr-3E8, pdCMV-dhfr-NV, pdCMV-dhfr-NI or pdCMV-dhfrC-3E8/BSM22.

The term "recombinant vector", as used herein, which describes an expression vector capable of expressing a protein of interest in a suitable host cell, refers to a genetic construct that comprises essential regulatory elements to which a gene insert is operably linked in such a manner as to be expressed in a host cell.

The term "operably linked", as used herein, refers to a functional linkage between a nucleic acid expression control sequence and a nucleic acid sequence coding for a target protein in such a manner as to allow general functions. The operable linkage to a recombinant vector may be prepared using a genetic recombinant technique well known in the art, and site-specific DNA cleavage and ligation may be easily achieved using enzymes generally known in the art.

A suitable expression vector in the present invention includes expression regulatory elements, such as a promoter, an initiation codon, a stop codon, a polyadenylation signal and an enhancer, as well as signal sequences for membrane targeting or secretion. The initiation and stop codons are generally considered to be a portion of a nucleotide sequence coding for an immunogenic target protein, are necessary to be functional in an individual to whom a genetic construct has been administered, and must be in frame with the coding sequence. Promoters may be generally constitutive or inducible. Non-limiting examples of promoters available in prokaryotic cells include lac, tac, T3 and T7 promoters. Non-limiting examples of promoters available in eukaryotic cells include simian virus 40 (SV40) promoter, mouse mammary tumor virus (MMTV) promoter, human immunodeficiency virus (HIV) promoter such as the HIV Long Terminal Repeat (LTR) promoter, moloney virus promoter, cytomegalovirus (CMV) promoter, epstein barr virus (EBV) promoter, rous sarcoma virus (RSV) promoter, as well as promoters from human genes such as human β-actin, human hemoglobin, human muscle creatine and human metallothionein.

An expression vector may include a selectable marker that allows selection of host cells containing the vector. Genes coding for products that confer selectable phenotypes, such as resistance to drugs, nutrient requirement, resistance to cytotoxic agents or expression of surface proteins, are used as general selectable markers. Since only cells expressing a selectable marker survive in the environment treated with a selective agent, transformed cells can be selected. Also, a replicable expression vector may include a replication origin, a specific nucleic acid sequence that initiates replication. Also, available are viruses (e.g., vaculovirus) or phage vectors, and vectors that are able to integrate into the genome of host cells, such as retrovirus vectors.

A whole antibody or antibody fragment may be produced using a vector system that simultaneously expresses a light chain and a heavy chain in a single vector, or a system that expresses a light chain and a heavy chain in two separate vectors. In the latter case, the two vectors are introduced into host cells by co-transformation or targeted transformation. In targeted transformation, cells transformed with a vector containing a light chain (or heavy chain) gene are selected, and the selected cells expressing the light chain (or heavy chain) are again transformed with a vector containing a heavy chain (light chain) gene to finally select cells expressing both light and heavy chains.

To construct an antibody in a Fab form, a vector into which genes coding for amino acids of a human light chain variable region (VL) and constant region (CL), and a human heavy chain variable region (VH) and a first constant region domain (CH1) is inserted is used. In the detailed practice, a pComb3HSS vector is used. A more preferred vector is pC3-Q in which an amino acid sequence EVQL (glutamic acid-valine-glutamine-leucine; SEQ ID NO:36) prior to an XhoI site of the vector is modified to QVQL (glutamine-valine-glutamine-leucine; SEQ ID NO:37) to retain the first amino acid residue of the heavy chain, glutamine, and/or a gene III is removed to express a soluble Fab. This vector possesses a lacZ promoter and OmpA and pelB signal peptides.

In a preferred aspect, the present invention provides pC3-Q-3C4 comprising a heavy chain variable region having an amino acid sequence represented by SEQ ID No. 2 and a light chain variable region having an amino acid sequence represented by SEQ ID No. 21, pC3-Q-3D5 comprising a heavy chain variable region having an amino acid sequence represented by SEQ ID No. 3 and a light chain variable region having an amino acid sequence represented by SEQ ID No. 21, pC3-Q-3E8 comprising a heavy chain variable region having an amino acid sequence represented by SEQ ID No. 4 and a light chain variable region having an amino acid sequence represented by SEQ ID No. 21, pC3-Q-NV comprising a heavy chain variable region having an amino acid sequence represented by SEQ ID No. 5 and a light chain variable region having an amino acid sequence represented by SEQ ID No. 21, pC3-Q-NI comprising a heavy chain variable region having an amino acid sequence represented by SEQ ID No. 6 and a light chain variable region having an amino acid sequence represented by SEQ ID No. 21, pC3-Q-3E8/BSM22 comprising a heavy chain variable region having an amino acid sequence represented by SEQ ID No. 4 and a light chain variable region having an amino acid sequence represented by SEQ ID No. 22, and the like.

To construct a whole antibody, a vector into which a gene coding for amino acid of human light chain variable region (VL) and constant region (CL) and human heavy chain variable region (VH) and all constant region domains (CH1, CH2 and CH3) is inserted is used. In the detailed practice of the present invention, pdCMV-dhfr having two expression units was used, which was constructed using pCMV-dhfr (KCTC 8671P: Korean Pat. Registration No. 162021). The vector possesses two CMV promoters, and heavy and light chains are expressed from respective promoters.

In a preferred aspect, the present invention provides pdCMV-dhfr-3C4 comprising a heavy chain variable region having an amino acid sequence represented by SEQ ID No. 2 and a light chain variable region having an amino acid sequence represented by SEQ ID No. 21, pdCMV-dhfr-3D5 comprising a heavy chain variable region having an amino acid sequence represented by SEQ ID No. 3 and a light chain variable region having an amino acid sequence represented by SEQ ID No. 21, pdCMV-dhfr-3E8 comprising a heavy chain variable region having an amino acid sequence represented by SEQ ID No. 4 and a light chain variable region having an amino acid sequence represented by SEQ ID No. 21, pdCMV-dhfr-NV comprising a heavy chain variable region having an amino acid sequence represented by SEQ ID No. 5 and a light chain variable region having an amino acid sequence represented by SEQ ID No. 21, pdCMV-dhfr-NI comprising a heavy chain variable region having an amino acid sequence represented by SEQ ID No. 6 and a light chain variable region having an amino acid sequence represented by SEQ ID No. 21, pdCMV-dhfrC-3E8/BSM22 comprising a heavy chain variable region having an amino acid sequence represented by SEQ ID No. 4 and a light chain variable region having an amino acid sequence represented by SEQ ID No. 22, and the like.

Among the recombinant vectors, the pdCMV-dhfr-3E8 vector expressing a whole antibody 3E8 was deposited at KCTC (Korean Collection for Type Cultures; 52, Oun-dong, Yusong-ku, Taejon, Korea) on Jun. 21, 2001 and assigned accession number KCTC 1039BP. The pdCMV-dhfrC-3E8/BSM22 vector expressing a whole antibody 3E8/BSM22 was deposited at KCTC on May 31, 2004 and assigned accession number KCTC 10647BP.

In yet another aspect, the present invention relates to transformants transformed with the recombinant vectors.

Host cells suitable for the vectors may be prokaryotic cells such as *Escherichia coli, Bacillus subtilis, Streptomyces, Pseudomonas, Proteus mirabilis* or *Staphylococcus*. Also, eukaryotic cells useful as host cells include lower eukaryotic cells, such as fungi (e.g., *Aspergillus* species) and yeasts (e.g., *Pichia pastoris, Saccharomyces cerevisiae, Schizosaccharomyces, Neurospora crassa*), and cells derived from higher eukaryotes, such as insect cells. Host cells may be also derived from plants and mammals. Preferred cells include, but are not limited to, COS7 cells (monkey kidney cells), NSO cells, SP2/0, CHO (Chinese hamster ovary) cells, W138, BHK (baby hamster kidney) cells, MDCK, myeloma cells, HuT 78 cells and 293 cells. CHO cells are preferred. The pdCMV-dhfr-3E8 vector of the present invention was transformed into CHO cells using Lipofectamine, thereby yielding a transformed cell line 9E8, which was deposited at KCTC on Jun. 21, 2001 and assigned accession number KCTC 1040BP. Also, the pdCMV-dhfrC-3E8/BSM22 vector of the present invention was transformed into CHO cells, thereby yielding a transformed cell line 4D12-B31, which was deposited at KCTC on May 31, 2004 and assigned accession number KCTC 10646BP.

In the present invention, "transformation" into host cells includes any method by which nucleic acids can be introduced into organisms, cells, tissues or organs, and, as known in the art, may be performed by selecting suitable standard techniques according to host cells. These methods include, but are not limited to, electroporation, protoplast fusion, calcium phosphate ($CaPO_4$) precipitation, calcium chloride ($CaCl_2$) precipitation, agitation with silicon carbide fiber, *agrobacterium*-mediated transformation, and PEG-, dextran sulfate-, lipofectamine- and desiccation/inhibition-mediated transformation.

In still another aspect, the present invention relates to a method of preparing the humanized antibody by culturing the transformant.

In the antibody preparation method, the culturing of transformant may be performed using suitable media under suitable culture conditions, which are known in the art. This culturing process may be easily adapted according to the strains selected by those skilled in the art.

The antibody obtained by culturing the transformant may be used in an unpurified form, or may be used after being purified using various general methods, which may be used separately or in combination, for example, dialysis, salt precipitation and chromatography. Among them, chromatography is most commonly used. Examples of chromatography include ion exchange chromatography, size exclusion chromatography, and affinity chromatography.

An antibody prepared by the aforementioned method has enhanced affinity to an antigen. The term "affinity" is the ability to specifically recognize and bind to a specific region of an antigen. High affinity as well as the specificity of an antibody for an antigen are critical elements in immune responses. In the present invention, a heavy chain variable region is randomly mutated to prepare humanized heavy chain library cells, and the library cells are subjected to a colony lift assay to select mutant clones having high antigen binding capacity. The selected clones were assessed for their affinity by competitive ELISA. Other various methods, for example, surface plasmon resonance technology (SRP), may be used to measure the affinity of an antibody to an antigen.

The term "$K_D$", as used herein, refers to a dissociation constant of specific antibody-antigen interaction, and has been used to measure the affinity of an antibody to an antigen. The present antibody prepared by the aforementioned method had much better capacity to bind to a TAG-72 antigen than the parent antibody AKA/HzK.

Thus, an antibody having enhanced affinity, prepared by the above method, may be useful for diagnosing and treating cancer. The antibodies may be provided as they are or contained in a composition.

In still another aspect, the present invention relates to a method of diagnosing cancer using the antibody.

The present antibody binds to TAG-72 with high affinity. Thus, the complex formation between TAG-72 and the antibody may be determined by quantitatively or qualitatively measuring the signal size of a detection label, thereby allowing diagnosis of cancer. Non-limiting examples of the label enabling quantitative or qualitative measurement of the formation of antigen-antibody complexes include enzymes, fluorescent substances, ligands, luminescent substances, microparticles, redox molecules and radioactive isotopes. In the present invention, immunohistochemistry revealed that the present antibody has very strong reactivity with colon cancer.

In addition, the antibodies of the present invention may be administered to a patient in a form of being conjugated to an imaging marker and then detected in order to diagnose human carcinomas or metastases thereof. Since the antibodies of the present invention have higher affinity to an antigen than do conventional antibodies and are further humanized antibodies, they are very suitable for administration to patients. Administration and detection of an antibody-imaging marker conjugate and a method of conjugating an antibody to an imaging marker are described many times in the literature (Goldenberg et al., 1978, New England J. Med. 298, 1384-1388; Goldenberg et al., 1983, J. Amer. Med. Assoc. 280, 630-635; Goldengerg et al., 1983, Gastroenterol. 84, 524-532; Siccardi et al., 1986, Cancer Res. 46, 4817-4822; Epenetos et al., 1985, Cancer 55, 984-987; Philben et al., 1986, Cancer 57, 571-576; Chiou et al., 1986, Cancer Inst. 76, 849-855; Colcher et al., 1983, Cancer Res., 43, 736-742; Colcher, E. et al., Laboratory Research Methods in Biology and Medicine Immunodiagnostics. New York, Alan R. Liss. pp. 215-258 (1983); Keenan, A. M. et al., 1984, J. Nucl. Med.

25, 1197-1203; Colcher D. et al., 1987, Cancer Res. 47, 1185-1189; Estaban, J. M. et al., 1987, Intl. J. Cancer 39, 50-59; Martin, D. T., et al., 1984, Curr. Surg. 41, 193-194; Martin, E. W. Jr. et al., 1986, Hybridoma 5, S97-S108; Martin, D. T. et al., 1985, Am. J. Surg. 150, 672-675; Meares et al., Anal. Biochem. 1984, 142, 68-78; and Krejcarek et al., 1977, Biochem. and Biophys. Res. Comm. 77, 581-585). The dosage may vary depending on the patient's age and weight. The dosage of the antibody-imaging marker conjugate should be an amount capable of effectively visualizing or detecting tumor sites distinct from normal tissues.

Examples of imaging markers which can be conjugated to the antibody are well known to those skilled in the art, and include substances which can be detected by diagnostic imaging using a gamma scanner, a hand held gamma probe or position emission tomography, and substances which can be detected by nuclear magnetic resonance imaging using a nuclear magnetic resonance spectrometer.

Suitable examples of substances which can be detected using a gamma scanner include radioactive isotopes, such as $^{125}$I, $^{131}$I, $^{123}$I, $^{11}$In, $^{105}$Rh, $^{153}$Sm, $^{67}$Cu, $^{67}$Ga, $^{177}$Lu, $^{186}$Re, $^{188}$Re and $^{99}$mTc. $^{125}$I, $^{123}$I, $^{153}$Sm and $^{99}$ mTC are preferred because they have low energy and are suitable for a broad range of detection. An example of a substance which can be detected using a nuclear magnetic resonance spectrometer is gadolinium (Gd).

In still another aspect, the present invention relates to an anticancer composition comprising the antibody.

The term "anticancer", as used herein, includes "prevention" and "treatment". The term "prevention" means all actions that suppress or delay cancer formation by administering a composition comprising the antibody of the present invention. The term "treatment" means all actions that make cancer symptoms better or beneficially change cancer progression by administering the present antibody.

Compared to the conventional antibody AKA/HzK, the antibodies of the present invention were retained at higher levels in athymic mice xenografted with human colon cancer and were present at high levels in the blood. When the present antibodies were administered to athymic mice bearing human colon cancer xenografts, mice survived for a much longer period of time in comparison with control mice.

Cancer which can be treated by the present composition includes all types of cancer expressing TAG-72. Since TAG-72 is expressed in a broad range of human carcinomas, the present composition may treat all types of TAG-72-expressing cancer. Examples of such types of cancer include colon cancer, ovarian cancer, stomach cancer, pancreatic cancer and breast cancer.

When used as a therapeutic antibody, the antibodies of the present invention may be linked to a known therapeutic agent by direct or indirect coupling (e.g., covalent bonding) through a linker, and administered to the body in antibody-therapeutic conjugates in order to treat cancer.

Non-limiting examples of therapeutic agents capable of being linked to the antibody include chemical therapeutic agents, radionuclides, immunotherapeutic agents, cytokines, chemokines, toxins, biological agents, enzyme inhibitors, and heterofunctional antibodies: (1) antibodies coupled to radionuclides, such as $^{131}$I, $^{90}$Y, $^{105}$Rh, $^{47}$Sc, $^{67}$Cu, $^{212}$Bi, $^{211}$At, $^{67}$Ga, $^{125}$I, $^{186}$Re, $^{188}$Re, $^{177}$Lu, $^{153}$Sm, $^{123}$I and $^{111}$In, which are described, for example, in Goldengerg et al., 1981, Cancer Res. 41, 4354-4360; (2) antibodies coupled to drugs or biological response modifiers, such as methotrexate, adriamycin and lymphokines such as interferon, which are described, for example, in Chabner et al., 1985, Cancer, Principles and Practice of Oncology, Philadelphia, Pa., J.B. Lippincott Co. Vol. 1, pp. 290-328; (3) antibodies coupled to toxins such as ricin, abrin and diphteria, which are described, for example, in Uhr et al., 1983, Monoclonal antibodies and Cancer, Academic Press, Inc., pp. 85-98; (4) heterofunctional antibodies, that is, antibodies coupled to other antibodies so that the complexes bind both to carcinoma and to effector cells (e.g., K cells (killer cells) such as T cells), which are described, for example, in Perez et al., 1986, J. Exper. Med. 163, 166-178; and Lau et al., 1985, Proc. Natl. Acad. Sci. (USA) 82, 8648-8652; and (5) native, i.e., non-conjugated or non-complexed, antibodies, which are described, for example, in Herlyn et al., 1982, Proc. Natl. Acad. Sci., (USA) 79, 4761-4765.

The anticancer composition includes an acceptable carrier and is formulated into a suitable dosage form according to administration modes. Pharmaceutical preparations suitable for administration modes are known, and generally include surfactants that facilitate transport across the membrane. Such surfactants may be derived from steroids, or may be cationic lipids such as N-[1-(2,3-dioleyloxy)propyl]-N,N,N-trimethylammonium chloride (DOTMA), or various compounds such as cholesterol hemisuccinate and phosphatidyl glycerol.

In still another aspect, the present invention relates to a method of treating cancer by administering the antibody.

The present composition may be administered to a patient in an amount sufficient for treating cancer. The dosage may vary according to a variety of factors, including type of cancer, the patient's age and weight, properties and severity of the illness, types of currently used therapy, treatment frequency, and administration modes and routes, and may be readily determined by specialists in the art. The present composition may be administered either simultaneously or sequentially with pharmaceutical or physiological ingredients, and may also be administered in combination with conventional therapeutic agents in a sequential or simultaneous manner. The present composition may be administered in a single or multiple dosage. Taking all of the factors into account, it is important to administer the composition in a minimal amount to achieve maximal effects without side effects, and such a dosage may be determined by those skilled in the art.

The term "administration", as used herein, means introduction of a predetermined amount of a substance into a patient by a certain suitable method. The composition comprising the antibody of the present invention may be administered via any of the common routes, as long as it is able to reach a desired tissue. A variety of modes of administration are possible, including intraperitoneally, intravenously, intramuscularly, subcutaneously, intradermally, orally, topically, intranasally, intrapulmonarily and intrarectally, but the present invention is not limited to these exemplified modes of administration. However, since proteins are digested upon oral administration, active ingredients of a composition for oral administration should be coated or formulated for protection against degradation in the stomach. In addition, the pharmaceutical composition may be administered using a certain apparatus that is capable of transporting the active ingredients into a target cell.

Hereinafter, the present invention will be described in detail.

First, a heavy chain variable region of an antibody specifically binding to TAG-72 according to the present invention was prepared.

A heavy chain variable region of the humanized antibody AKA/HzK has an amino acid sequence represented by SEQ ID No. 1, and consists of an FR1 spanning positions 1 to 30, a CDR1 spanning positions 31 to 35, an FR2 spanning positions 36 to 49, a CDR2 spanning positions 50 to 66, an FR3 spanning positions 67 to 98, a CDR3 spanning positions 99 to 104, and an FR4 spanning positions 105 to 115. Among them, the CDR3 was mutated to certain other amino acids to construct a novel antibody having higher antigen binding capacity to TAG-72 than does the parent antibody AKA/HzK.

In the heavy chain variable region of the humanized antibody AKA/HzK, which has the amino acid sequence of SEQ ID No. 1, the CDR3 was randomly mutated at a serine (Ser) residue at position 99, a leucine (Leu) residue at position 100, an asparagine (Asn) residue at position 101, a methionine (Met) residue at position 102, and an alanine (Ala) residue at position 103. In detail, PCR was carried out using as a template a gene expression vector pC3-Q-AKA/HzK for the humanized antibody AKA/HzK, which was prepared by replacing the threonine residue at position 97 of a heavy chain variable region of a pC3-Q-HzCC49Fab-1-dgIII vector (Korean Pat. Registration No. 0318761) with alanine, with primers including a sequence in which the heavy chain CDR3 is mutated, in order to obtain DNA fragments containing a mutated CDR 3 (FIG. 1). The DNA fragments thus obtained and a pC3-Q-AKA/HzK vector were individually digested with XhoI and ApaI, purified, and ligated. The ligated DNA molecules were transformed into Electro-Ten blue $E.$ $coli$ competent cells (Stratagene, USA).

In order to construct a novel antibody having enhanced antigen binding affinity for TAG-72, a colony lift assay was performed three times using $E.$ $coli$ containing the humanized heavy chain library (J. Immunol. Meth. 272: 219-233, 2003). Clones isolated by primary, secondary and tertiary screens were assessed to determine whether they have better antigen binding capacity than AKA/HzK Fab by competitive ELISA using biotin-conjugated AKA/HzK Fab. The evaluation of the antigen binding capacity of the selected clones resulted in the finding that a mutant in which the asparagine residue at position 97 is replaced with a nonpolar amino acid, preferably isoleucine or valine, has better antigen binding capacity than AKA/HzK.

Mutant clones isolated according to the above procedure were designated 3C4, 3D5, 3E8, NV and NI, respectively. DNA sequencing of heavy chain variable regions of the mutant clones revealed that they have amino acid sequences represented by SEQ ID Nos. 2, 3, 4, 5 and 6, respectively (FIG. 3).

In order to convert an antibody in a Fab form to a whole IgG form, variable regions of heavy and light chains were inserted into an expression vector for a whole IgG form by a general recombination method. First, a signal sequence of an antibody gene was linked with a variable region of the mutant by recombinant PCR. The resulting DNA fragment was inserted into the same restriction sites of a heavy chain gene in an expression vector pdCMV-dhfr-AKA/HzK (Korean Pat. No. 0318761) for a whole IgG form of the humanized antibody AKA/HzK to construct a plasmid expressing an antibody in a whole IgG form. Among the resulting expression plasmids, pdCMV-dhfr-3E8 was deposited at KCTC (Korean Collection for Type Cultures; 52, Oun-dong, Yusong-ku, Taejon, Korea) on Jun. 21, 2001 and assigned accession number KCTC 1039BP.

The expression vectors were individually transformed into CHO cells to obtain a transformant. DHFR-deficient CHO cells were subcultured, transformed with the whole antibody expression vector using Lipofectamine, and selected in a selection medium containing G418 and another selection medium containing MTX. The surviving cell clones were then isolated, thereby establishing cell lines transformed with the present vectors expressing a mutant antibody. Among them, a transformed cell line 9E8 transformed with pdCMV-dhfr-3E8 was deposited at KCTC (Korean Collection for Type Cultures; 52, Oun-dong, Yusong-ku, Taejon, Korea) on Jun. 21, 2001 and assigned accession number KCTC 1040BP.

Antibodies expressed by the transformed cell lines were assessed for their antigen binding affinity to determine whether they are available for the diagnosis and treatment of cancer. As a result, the antibodies prepared by the present method all had greatly increased affinity in comparison with the conventional antibody AKA/HzK. The antigen binding affinity ($K_D$) of each antibody was found to be $1.45 \times 10^{-8}$ M for the AKA/HzK antibody, $1.33 \times 10^{-9}$ M for the whole antibody 3C4, $2.27 \times 10^{-9}$ M for the whole antibody 3D5, and $0.65 \times 10^{-9}$ M for the whole antibody 3E8. When the antigen binding affinity of the mutant antibodies of the present invention was compared with that of AKA/HzK, the present antibodies had the $K_D$ values 11, 6 and 22-fold higher than AKA/HzK, which had a $K_D$ value of $1.45 \times 10^{-8}$ M. The $K_D$ values of the whole antibodies NV and NI were $1.66 \times 10^{-9}$ M and $3.38 \times 10^{-9}$ M, respectively, which were about 8 and 4-fold, respectively, higher than the $1.45 \times 10^8$ M of AKA/HzK.

Subsequently, a humanized light chain of 3E8 was replaced with a certain human light chain in order to construct an antibody having excellent antigen binding capacity against TAG-72 and a reduced risk of immune responses in comparison with the 3E8 antibody when administered to the body. For this, a novel antibody was constructed by replacing the light chain variable region represented by SEQ ID No. 21 with a light chain of human antibodies.

A human light chain library was prepared from human peripheral blood lymphocytes (PBL) to select a human light chain capable of replacing a light chain of the humanized antibodies of the present invention. In detail, total RNA was isolated from human PBL, and human light chain cDNA was selectively synthesized using the isolated total RNA as a template PCR was then carried out using the synthesized cDNA as a template with 5'-specific primers for a human kappa light chain variable region and a 3'-specific primer for a human kappa light chain constant region to selectively amplify a human antibody light chain gene. DNA fragments obtained by the PCR and a pC3-Q-3E8 vector were individually digested with SacI and XbaI, purified, ligated, and transformed into Electro-Ten blue $E.$ $coli$ competent cells.

In order to construct a novel antibody having enhanced antigen binding affinity for TAG-72, a colony lift assay was performed three times using $E.$ $coli$ containing the human light chain library. Clones isolated by primary, secondary and tertiary screens were assessed to determine whether they have better antigen binding capacity than 3E8 Fab by competitive ELISA using biotin-conjugated 3E8 Fab.

The clones thus selected were assessed for their antigen binding capacity to isolate clones having antigen binding capacity similar to that of 3E8 Fab. The evaluation of Fab antibodies purified from the isolated clones resulted in the finding that a clone has higher antigen binding capacity than the 3E8 Fab of the present invention. This clone was designated "pC3-Q-3E8/BSM22". The DNA sequencing of the light chain variable region of the 3E8/BSM22 clone revealed that the clone has an amino acid sequence represented by SEQ ID No. 22, which is encoded by a nucleic acid sequence of SEQ ID No. 23.

In order to prepare a humanized antibody in a whole IgG form containing a human light chain variable region, a light chain variable region gene having a nucleic acid sequence of SEQ ID No. 23 was cloned into the cloned site of a light chain variable region gene of an expression vector of the humanized antibody 3E8, pdCMV-dhfr-3E8.

A BsiWI restriction enzyme recognition sequence was introduced into a site between a variable region and a constant region to clone only a variable region gene in a light chain gene of the expression vector pdCMV-dhfr-3E8, thereby yielding a cassette vector pdCMV-dhfrC-3E8. Then, a signal sequence of an antibody gene was ligated with a human light chain variable region sequence, contained in the pC3-Q-3E8/BSM22 vector, by recombinant PCR. The ligated DNA was subcloned into HindIII/BsiWI sites of pdCMV-dhfrC-3E8 using HindIII and BsiWI restriction enzymes, thereby yielding pdCMV-dhfrC-3E8/BSM22. The pdCMV-dhfrC-3E8/BSM22 plasmid was deposited at KCTC on May 31, 2004 and assigned accession number KCTC 10647BP.

The expression plasmid of the present invention, prepared as above using Lipofectamine, was introduced into animal cells to express whole IgG in the animal cells.

The antigen binding affinity of an antibody expressed by the transformed animal cells was measured by competitive ELISA and compared with that of the 3E8 antibody of the present invention. The 3E8/BSM22 antibody was found to have better antigen binding capacity than the 3E8 antibody (FIG. 9). In detail, the 3E8/BSM22 antibody had a $K_D$ of about $0.45 \times 10^{-9}$ M, and the 3E8 antibody had a $K_D$ of $0.65 \times 10^{-9}$ M. The 3E8/BSM22 antibody was found to have an antigen binding affinity about 1.5-fold higher than the 3E8 antibody.

The expression plasmid pdCMV-dhfrC-3E8/BSM22 of the present invention, prepared as described, was transfected into dhfr-deficient CHO cells, and selected in a selection medium containing G418 and another selection medium containing MTX. The surviving cell clones were then isolated, thereby establishing a cell line 4D12-B31 transformed with the pdCMV-dhfrC-3E8/BSM22 expression vector of the present invention. The transformed cell line was deposited at KCTC (Korean Collection for Type Cultures; 52, Oun-dong, Yusong-ku, Taejon, Korea) on May 31, 2004 and assigned accession number KCTC 10646BP.

As apparent from the above results, the novel antibodies of the present invention are humanized antibodies having excellent antigen binding affinity and a reduced risk of immune responses, and thus are useful in the diagnosis and treatment of cancer.

A better understanding of the present invention may be obtained through the following examples which are set forth to illustrate, but are not to be construed as the limit of the present invention.

EXAMPLE 1

Preparation of AKA Humanized Heavy Chain CDR3 Library

A novel humanized antibody having enhanced antigen binding affinity in comparison with a humanized antibody AKA was prepared as follows. First, the amino acid sequence of the humanized heavy chain HCDR3 of the AKA antibody, which is represented by SEQ ID No. 1, was randomly mutated at a serine (Ser) residue at position 99, a leucine (Leu) residue at position 100, an asparagine (Asn) residue at position 101, a methionine (Met) residue at position 102, and an alanine (Ala) residue at position 103 (FIG. 1).

In detail, PCR was carried out using as a template a gene expression vector pC3-Q-AKA/HzK (Korean Pat. Registration No. 318761) for the humanized antibody AKA with a pair of VH135 and HCDR3BACK primers, represented by SEQ ID Nos. 7 and 8, respectively, and another pair of HCDR3FORWARD and LHS11 primers, represented by SEQ ID Nos. 9 and 10, respectively. PCR was carried out using Taq DNA polymerase under conditions that included pre-denaturation at 95° C. for 3 min and 25 cycles of denaturation at 95° C. for 50 sec, annealing at 55° C. for 50 sec and elongation at 72° C. for 1 min. A DNA fragment of 296 bp, obtained by PCR using the primer pair of VH135 and HCDR3BACK, and another DNA fragment of 180 bp, obtained by PCR using the primer pair of HCDR3FORWARD and LHS11, were annealed, and subjected to recombinant PCR using VH135 and LHS11 primers, thereby yielding a DNA fragment of 458 bp. The recombinant PCR was carried out using Taq DNA polymerase under conditions that included pre-denaturation at 95° C. for 3 min and 25 cycles of denaturation at 95° C. for 50 sec, annealing at 55° C. for 50 sec and elongation at 72° C. for 1 min. A DNA fragment obtained by the recombinant PCR and a pC3-Q-AKA/HzK vector were individually digested with XhoI and ApaI and purified. The two digested DNA fragments were ligated at 16° C. overnight and incubated at 70° C. for 10 min to inactivate ligase. Then, the reaction mixture was supplemented with 20 μl of glycogen and 20 μl of 3 M sodium acetate and then ethanol, and was placed at −20° C. overnight to precipitate DNA. The precipitated DNA was washed with 70% ethanol, dried, and suspended in 20 μl of distilled water. The ligated DNA thus obtained was transformed into Electro-Ten blue *E. coli* competent cells by electroporation. In detail, Electro-Ten blue cells were incubated with agitation in 500 ml of 2×YT at 37° C. until the culture reached an OD (optimal density) value of about 0.5 to 0.7, and placed on ice for 30 min. The cells were centrifuged at 4000 rpm at 4° C. for 15 min. After the supernatant was discarded, the cell pellet was suspended in 500 ml of 10% glycerol. The cell suspension was centrifuged at 5000 rpm at 4° C. for 15 min. After the supernatant was discarded, the cell pellet was suspended in 250 ml of 10% glycerol and centrifuged again at 5000 rpm at 4° C. for 15 min. After the supernatant was discarded, the cell pellet was suspended in 20 ml of 10% glycerol and centrifuged again at 4000 rpm at 4° C. for 15 min. After the supernatant was discarded, the cell pellet was suspended in 1-2 ml of 10% glycerol, thereby yielding competent cells. 300 μl of the competent cells were aliquotted into 1.5 ml tubes and stored at −70° C.

EXAMPLE 2

Selection of Mutant Clones Having Excellent Antigen Binding Capacity

In order to find a novel humanized antibody specifically binding to TAG-72, the library cells prepared in Example 1 were screened by a colony lift assay (Radosevic et al., J. Immunol. Methods, 2003, 272(1-2), 219-233) (FIG. 2).

First, a nitrocellulose membrane was placed onto a 2×YTA plate, and about $1 \times 10^6$ cells were smeared onto the membrane and cultured overnight. The membrane is called a master membrane.

During the overnight culture, a capture membrane for finding cells having strong antigen binding capacity was coated with 10 μg/ml of TAG-72-positive BSM (bovine submaxillary mucin, type-1-S, Sigma), in PBS (phosphate buffered saline) at 37° C. for 6 hrs. The membrane was washed with PBS twice and incubated in 5% skim milk at 37° C. for 2 hrs. After the skim milk was removed, the membrane was wet with 2×YT medium supplemented with 100 μg/ml of ampicillin and 1 mM IPTG (isopropyl-β-D-thiogalactopyranoside). After the capture membrane was placed onto a 2×YT plate supplemented with 100 µg/ml of ampicillin and 1 mM IPTG, the master membrane onto which library cells were smeared was placed onto the capture membrane and incubated at room temperature for 16-24 hrs.

The capture membrane was washed with 0.05% Tween 20-containing PBS (PBST) five times and incubated in skim milk in PBS at 37° C. for 6 hrs. To select clones bound to the BSM antigen, the capture membrane was incubated in a 1:1000 dilution of horseradish peroxidase-conjugated anti-human F(ab')2 antibody at 37° C. for 1 hr. The capture membrane was washed with PBST about five times to eliminate unbound antibody molecules, and developed using the ECL method to assess the antigen binding capacity of cells.

Cells identified to have the binding affinity for TAG-72 were collected at the same positions of the master membrane and incubated in 2×YTA at 37° C. until the culture reached an OD value of about 0.7. A colony lift assay was carried out using the cultured cells according to the same procedure. Then, competitive ELISA was performed to determine whether Fab clones obtained by primary, secondary and tertiary screens have higher binding affinity for TAG-72 than does wild-type AKA/HzK Fab.

For use in competitive ELISA, E. coli Fab clones obtained in the third screening were incubated with agitation at 37° C. When the culture reached an OD value of 0.5 to 1.0, the cells were treated with 1 mM IPTG at 30° C. overnight to induce Fab expression. The culture supernatants were collected. In order to determine whether the Fab antibodies have excellent antigen binding capacity in comparison with the wild-type AKA/HzK Fab, each well of an ELISA plate was coated with 1 µg of BSM overnight, blocked with 2% BSA, and washed with TBS-T three times. 25 µl of a 1:2000 dilution of a biotin-conjugated wild-type AKA/HzK Fab antibody (1 mg/ml) and 25 µl of each of the obtained Fab antibodies were added to one well, and the plate was incubated at 37° C. for 1 hr and washed with TBS-T to eliminate antibody molecules not bound to the antigen. To determine the relative amount of biotinylated AKA/HzK Fab binding to TAG-72, 50 µl of a 1:1000 dilution of streptavidin-alkaline phosphatase capable of binding biotin was added to each well, followed by incubation at 37° C. for 30 min. The plate was washed with TBS-T three times to remove unbound streptavidin-alkaline phosphatase, and developed with 50 µl of a para-nitrophenylphosphate solution for at least 20 min. Absorbance was then measured at 405-450 nm. Herein, as positive controls, AKA/HzK Fab was used in 5 µg/ml and 10 µg/ml, and 2% BSA was used alone as a negative control. As a result of competitive ELISA, mutant clones displaying lower ELISA values than did the AKA/HzK as a control were selected and estimated for their antigen binding capacity in the following Example 3.

EXAMPLE 3

Evaluation of Antigen Binding Capacity of Mutant Clones

In order to determine the antigen binding capacity of Fab from each clone selected in Example 2, the mutant clones were cultured with agitation at 37° C. When the culture reached an OD value of 0.5 to 1.0, the cells were treated with 1 mM IPTG at 30° C. overnight to induce Fab expression. The cells were harvested and subjected to an osmotic shock using TES buffer (0.2 M Tris-HCl, pH 8.0, 0.5 mM EDTA, 0.5 M sucrose) to obtain a periplasmic extract in which a mutant Fab antibody was dissolved.

In order to investigate the antigen binding specificity and capacity of the mutant Fab, each well of an ELISA plate was coated with 1 µg of BSM and 1 µg of BSA overnight, blocked with 2% BSA and washed with TBS-T four times. The Fab antibody present in the periplasmic extract was added to each well, and the plate was incubated at 37° C. for 1 hr and washed with TBS-T buffer to remove antibody molecules not bound to the antigen. The plate was then incubated in a secondary antibody, anti-human F(ab')$_2$ IgG HRP, diluted in TBS-T. OPD/H$_2$O$_2$ substrate was added to each well to develop color, and absorbance was measured at 492 nm.

Clones having remarkably enhanced antigen binding capacity compared to the wild-type AKA/HzK Fab were isolated. A full-length nucleotide sequence of the HCDR3 of each mutant clone was determined using a T7 Sequenase V2.0 DNA sequencing kit (Amersham). The determined nucleotide sequences were found to encode amino acid sequences represented by SEQ ID Nos. 2, 3, 4, 5 and 6, respectively (see, FIG. 3). The obtained Fab mutants were designated 3C4, 3D5, 3E8, NV and NI, respectively, and expression vectors thereof were designated pC3-Q-3C4, pC3-Q-3D5, pC3-Q-3E8, pC3-Q-NV and pC3-Q-NI, respectively.

EXAMPLE 4

Construction of Expression Plasmids for Expression of Whole IgG of Humanized Clones In order to prepare an antibody in a whole IgG form using the Fab mutant 3E8, a signal sequence of an antibody gene, a variable region of the Fab mutant and a constant region of human antibodies were ligated by recombinant PCR (FIG. 4).

In detail, to synthesize a signal sequence of an antibody gene, PCR was carried out using as a template an expression vector pdCMV-dhfr-AKA/HzK for the humanized antibody AKA/HzK in whole IgG form with a primer pair of LHS39 and LHS43, represented by SEQ ID Nos. 11 and 12, respectively. As a result, a DNA fragment of 96 bp was obtained.

In addition, to synthesize the 5' region of a heavy chain variable region gene of the Fab mutant, PCR was carried out using as templates pC3-Q-3C4, pC3-Q-3D5, pC3-Q-3E8, pC3-Q-NV and pC3-Q-NI vectors with a primer pair of LHS44 and Type C Back, represented by SEQ ID Nos. 13 and 14, respectively. As a result, a DNA fragment of 306 bp was obtained. Also, to synthesize the 3' region of the heavy chain variable region gene, PCR was carried out using as templates pC3-Q-3C4, pC3-Q-3D5, pC3-Q-3E8, pC3-Q-NV and pC3-Q-NI vectors with a primer pair of Type C Forward, as a forward primer, and LHS 11, as a reverse primer, represented by SEQ ID Nos. 15 and 10, respectively. PCR was carried out using Taq DNA polymerase under conditions that included pre-denaturation at 95° C. for 3 min and 25 cycles of denaturation at 94° C. for 50 sec, annealing at 55° C. for 50 sec and elongation at 72° C. for 1 min. As a result, a DNA fragment of 159 bp was obtained. Thereafter, PCR was carried out using the three DNA fragments (96 bp, 306 bp and 159 bp) as templates with LHS11 and LHS39 primers, represented by SEQ ID Nos. 10 and 11, respectively, to ligate the three DNA fragments, thereby yielding a DNA fragment of 531 bp. The ligated DNA was digested with EcoRI and ApaI at each end thereof, and inserted into EcoRI/ApaI sites of an animal expression vector pdCMV-dhfr-AKA/HzK carrying a gene encoding a conventional humanized antibody AKA/HzK. The resulting expression plasmids were designated pdCMV-dhfr-3C4, pdCMV-dhfr-3D5, pdCMV-dhfr-3E8, pdCMV-dhfr-NV and pdCMV-dhfr-NI. Among them, the pdCMVdhfr-3E8 plasmid was deposited at KCTC (Genetic Resources Center, KRIBB, Korea) and assigned accession number KCTC 1039BP.

EXAMPLE 5

Determination of Antigen Binding Affinity of Humanized Antibodies

In order to determine antigen binding capacity and antigen binding affinity of the antibodies prepared as above, the expression plasmids of the present invention, prepared in Example 4, were introduced into animal cells to produce whole IgG antibodies.

First, COS7 cells were subcultured in DMEM medium (GIBCO) supplemented with 10% fetal bovine serum (FBS) in a 5% $CO_2$ incubator at 37° C. The cells were plated onto 100-mm culture dishes at a density of $1\times10^6$ cells/ml, cultured at 37° C. overnight, and washed with OPTI-MEM I medium (GIBCO) three times. Separately, 5 μg of each of the antibody expression vectors, pdCMV-dhfr-3C4, pdCMV-dhfr-3D5, pdCMV-dhfr-3E8, pdCMV-dhfr-NV and pdCMV-dhfr-NI, prepared in Example 4, were diluted with 500 μl of OPTI-MEM I. 25 μl of Lipofectamine (GIBCO) were also diluted with 500 μl of OPTI-MEM I. The diluted expression vector was mixed with the diluted Lipofectamine in a 15-ml tube and allowed to stand at room temperature for more than 15 min to form DNA-Lipofectamine complexes. The DNA-Lipofectamine mixture was supplemented with 5 ml of OPTI-MEM I and applied to the washed COS7 cells. The cells were cultured for 48 hrs in a 5% $CO_2$ incubator at 37° C. to express 3C4, 3D5, 3E8, NV and NI antibodies of the present invention.

The antigen binding capacity and antigen binding affinity of 3C4, 3D5, 3E8, NV and NI antibodies obtained from cell culture supernatants were measured by ELISA. First, 250 ng of BSM were placed into each well of an immunoplate, and the immunoplate was incubated at 4° C. overnight to allow an antigen to attach to the bottom of the plate. The immunoplate was then blocked with 2% BSA and washed with TBS-T four times. The culture supernatants of COS7 cells, containing the expressed whole IgG mutants, were diluted in PBS and added to each well of the plate in the same concentration. The plate was incubated at 37° C. for 30 min and washed with TBS-T to remove antibody molecules not bound to the antigen. The primary antibody was reacted with a secondary antibody, anti-human IgG(Fc specific)-HRP, diluted 1:5000 in TBS-T. OPD/$H_2O_2$ substrate was added to each well to develop color, and absorbance was measured at 492 nm.

In order to compare the antigen binding affinity of the 3E8 antibody with that of AKA/HzK, competitive ELISA was carried out. Various concentrations of a competitive antigen were mixed with submaximal concentrations of 3C4, 3D5, 3E8, NV, NI or AKA/HzK antibodies, and allowed to react at 37° C. for 3 hrs. The reaction mixture was added to each well of an ELISA plate whose wells were precoated with 250 ng of the TAG-72 antigen. After reaction for 30 min, the plate was incubated in anti-human IgG(Fc specific)-HRP, and the degree of color development was measured.

The antigen binding affinity ($K_D$) of antibodies was found to be $1.45\times10^{-8}$ M for AKA/HzK, $1.33\times10^{-9}$ M for 3C4, $2.27\times10^{-9}$ M for 3D5, $0.65\times10^{-9}$ M for 3E8, $1.66\times10^{-9}$ M for NV, and $3.38\times10^{-9}$ M for NI. These results indicate that the mutant antibodies respectively have about 11, 6, 22, 8 and 4-fold enhanced antigen binding affinity in comparison with AKA/HzK, having a KD value of $1.45\times10^{-8}$M (FIG. 5$a$, 5$b$).

EXAMPLE 6

Establishment of 3E8 Antibody-expressing Cell Line

A CHO cell line transformed with an expression vector of the 3E8 antibody, pdCMV-dhfr-3E8, was established to produce the 3E8 antibody.

First, a DHFR-minus CHO cell line, DG44 (ATCC CRL 9096), was subcultured in 10% FBS-containing DMEM medium (GIBCO) in a 5% $CO_2$ incubator at 37° C. The cells were plated onto a 100-mm culture dish at a density of $1\times10^6$ cells/ml, cultured at 37° C. overnight, and washed with OPTI-MEM I medium (GIBCO) three times. Separately, 5 μg of the antibody expression vector pdCMV-dhfr-3E8, prepared in Example 4, was diluted with 500 μl of OPTI-MEM I. 25 μl of Lipofectamine (GIBCO) were also diluted with 500 μl of OPTI-MEM I. The diluted expression vector was mixed with the diluted Lipofectamine in a 15-ml tube and allowed to stand at room temperature for more than 15 min to form DNA-Lipofectamine complexes. The DNA-Lipofectamine mixture was supplemented with 5 ml of OPTI-MEM I and applied to the washed DG44 cells. The cells were cultured for 6 hrs in a 5% $CO_2$ incubator at 37° C., and supplemented with 3 ml of 20% bovine calf serum-containing DMEM/F12 medium and further cultured for 48 hrs under the same conditions. The cells transformed with the mutant antibody expression vector were detached, suspended in a density of $1\times10^4$ cells/ml in a selection medium, prepared by adding 10% dialyzed FBS and 550 μg/ml of G418 to MEM-A medium not containing nucleotides, and aliquotted into 96-well plates. After a culture period of more than one week, formed colonies were assessed for antibody production by ELISA to select clones expressing the antibody at high concentrations.

ELISA was carried out as follows. 100 ng of anti-human IgG was placed into each well of an immunoplate, and the immunoplate was incubated at 4° C. overnight. The immunoplate was then blocked with 2% BSA and washed with TBS-T four times. The culture supernatants were diluted in PBS and added to each well of the plate. The plate was incubated at 37° C. for 1 hr and washed with TBS-T to remove antibody molecules not bound to the antibody. The primary antibody was reacted with a secondary antibody, anti-human IgG(Fc specific)-HRP, diluted 1:5000 in TBS-T. OPD/$H_2O_2$ substrate was added to each well to develop color, and absorbance was measured at 492 nm.

The selected clones secreting the 3E8 antibody in high concentrations were cultured in a medium containing 20 nM MTX for 2 weeks, and then cultured in a selection medium containing 80 nM MTX. A clone expressing the highest concentration of the 3E8 antibody was designated "9E8 cell line", which was deposited at KCTC (Korean Collection for Type Cultures; 52, Oun-dong, Yusong-ku, Taejon, Korea) on Jun. 21, 2001 and assigned accession number KCTC 1040BP.

EXAMPLE 7

Purification of Whole IgG Mutants and Evaluation of Their Antigen Binding Affinity The 9E8 cell line, prepared in Example 6, was cultured in a serum-free medium, CHO-S-SFMII (Gibco). The culture supernatant was run through a Protein G-Sepharose 4B column (Pharmacia). Antibodies bound to the column were eluted with 0.1 M glycine (pH 7.0), neutralized with 1.0 M Tris (pH 9.0) and dialyzed in PBS (pH 7.0). The purified 3E8 antibody was electrophoresed on a 10% SDS-polyacrylamide gel.

As shown in FIG. 6, when the antibody was separated on SDS-PAGE under reduction conditions, two protein bands were detected at 55 kDa and 25 kDa, which are known to be the molecular weights of heavy and light chains, respectively (see, lane 1). These results indicate that the 9E8 cell line of the present invention produces a whole antibody that is in a tetrameric form.

In addition, when the antigen binding affinity of the purified 3E8 antibody was measured according to the same method as in Example 5, it was found to be about $0.65 \times 10^{-9}$ M.

EXAMPLE 8

Preparation of Human Light Chain Library

In order to prepare a novel antibody having a lower risk of HAMA responses than the humanized antibody 3E8 and retaining the antigen binding capacity of 3E8, a humanized light chain of the 3E8 antibody was replaced with a human light chain. First, a human light chain library was prepared from human PBL (peripheral blood lymphocytes) using a method described by Hofman et al. (Hofman et al., 1982, Am. J. Clin. Pathol., 77(6):710-713).

In detail, total RNA was isolated from human PBL, and human light chain cDNA was selectively synthesized using the isolated total RNA as a template, reverse transcriptase (Superscript II, Gibco BRL) and a CK1d primer represented by SEQ ID No. 24. PCR was then carried out using the synthesized cDNA as a template with, 5'-specific primers (VK1, VK2, VK3, VK4 and VK5) for a human kappa light chain variable region, represented by SEQ ID Nos. 25 to 29, paired with a CK1d primer to selectively amplify a human antibody light chain gene.

PCR was carried out using Taq DNA polymerase under conditions that included pre-denaturation at 95° C. for 5 min and 20 cycles of denaturation at 95° C. for 50 sec, annealing at 55° C. for 50 sec and elongation at 72° C. for 1 min. The 20 PCR cycles were determined to increase the diversity of human antibodies.

The human light chain DNA fragments obtained by the PCR were digested with SacI and XbaI, and inserted into SacI/XbaI sites of an expression vector for Fab of the humanized antibody 3E8 of the present invention, pC3-Q-3E8.

In detail, the pC3-Q-3E8 vector was digested with SacI and XbaI, purified, ligated with the DNA fragments obtained by the PCR at 16° C. overnight, and incubated at 70° C. for 10 min to inactivate ligase. Then, the reaction mixture was supplemented with glycogen and 3 M sodium acetate and then ethanol, and was placed at -20° C. overnight to precipitate DNA. The precipitated DNA was washed with 70% ethanol, dried, and suspended in 20 μl of distilled water. The ligated DNA thus obtained was transformed into Electro-Ten blue E. coli competent cells by electroporation.

EXAMPLE 9

Selection of 3E8/BSM22 Mutant Clone Having Strong Antigen Binding Capacity

In order to find a novel antibody binding to TAG-72 from the library cells prepared in Example 8, a colony lift assay was performed as described in Example 2.

In order to determine whether cell clones showing antigen binding capacity have better antigen binding capacity than the wild-type 3E8 Fab, competitive ELISA was carried out using a biotin-conjugated 3E8 Fab antibody as described in Example 2. As a result, mutant clones having lower ELISA values than 3E8 Fab as a control were obtained.

Each clone was assessed for its antigen binding capacity as described in Example 3. As a result, clones having better antigen binding capacity than the 3E8 Fab were isolated. The nucleotide sequence of a light chain variable region of each mutant clone was determined using a T7 Sequenase V2.0 DNA sequencing kit (Amersham). The determined nucleotide sequence was found to encode an amino acid sequence represented by SEQ ID No. 22 (FIG. 7). The obtained Fab mutant was designated 3E8/BSM22, and an expression vector thereof was designated pC3-Q-3E8/BSM22.

EXAMPLE 10

Construction of Expression Vector of 3E8/BSM22 Antibody in Whole IgG Form

In order to prepare the 3E8/BSM22 antibody in a whole IgG form containing a human light chain of the 3E8/BSM22 antibody, the human light chain gene was cloned into the cloned site of a light chain gene of an expression vector of the humanized antibody 3E8 of the present invention, pdCMV-dhfr-3E8.

First, a BsiWI restriction enzyme recognition sequence was introduced into a site between a variable region and a constant region to clone only a variable region gene in a light chain gene of the expression vector pdCMV-dhfr-3E8, thereby yielding a cassette vector pdCMV-dhfrC-3E8 (FIG. 8). In detail, PCR was carried out using pdCMV-dhfr-3E8 as a template with a primer pair of LHS42, represented by SEQ ID No. 30, and KCBsiWIback and another primer pair of KCBsiWIfor, represented by SEQ ID No. 32, and CK1d. The two PCR products were ligated by recombinant PCR using primers, LHS42, represented by SEQ ID No. 30, and CK1d. The resulting DNA fragment was digested with HindIII and XbaI and inserted into the site of the light chain gene of the pdCMV-dhfr-3E8 vector while replacing the light chain gene, thereby yielding pdCMV-dhfrC-3E8 (FIG. 8).

Then, a signal sequence of a light chain gene was ligated with a variable region sequence of the BSM22 vector by recombinant PCR. In detail, to amplify a signal sequence of an antibody gene, PCR was carried out using pdCMV-dhfr-AKA/HzK as a template with a primer pair of LHS42 and KcleaderBack, represented by SEQ ID Nos. 30 and 33, respectively. Also, to amplify a human light chain variable region gene of the Fab, PCR was carried out using pC3-Q-3E8/BSM22 as a template with a primer pair of KCfor and KCBsiWIback, represented by SEQ ID Nos. 34 and 31, respectively. To ligate the signal sequence and the human light chain variable region gene, recombinant PCR was carried out using LHS42 and KCBsiWIback primers, represented by SEQ ID Nos. 30 and 31, respectively. The recombinant PCR was carried out using Taq DNA polymerase under conditions that included pre-denaturation at 95° C. for min and 30 cycles of denaturation at 94° C. for 50 sec, annealing at 55° C. for 50 sec and elongation at 72° C. for 1 min.

The resulting DNA fragment was digested with HindIII and BsiWI, and inserted into HindIII/BsiWI sites of the animal expression vector pdCMV-dhfrC-3E8, thereby yielding an expression plasmid pdCMV-dhfrC-3E8/BSM22. The pdCMV-dhfrC-3E8/BSM22 plasmid was deposited at KCTC (Korean Collection for Type Cultures; 52, Oun-dong, Yusong-ku, Taejon, Korea) on May 31, 2004 and assigned accession number KCTC 10647BP.

EXAMPLE 11

Evaluation of Antigen Binding Affinity of 3E8/BSM22 Antibody

The antigen binding affinity of the 3E8/BSM22 antibody of the present invention was determined as follows. The expression plasmid pdCMV-dhfrC-3E8/BSM22 of the present invention was introduced into COS7 cells as described in Example 5 to produce the antibody in a whole IgG form. The antigen binding affinity of the expressed 3E8/BSM22 antibody present in the culture supernatant was measured by competitive ELISA. The 3E8/BSM22 antibody displayed a $K_D$ of about $4.5 \times 10^{-10}$ M, and the 3E8 antibody showed a $K_D$ of about $5 \times 10^{-10}$ M. Thus, the 3E8/BSM22 antibody was found to have an antigen binding affinity about 1.5-fold higher than the 3E8 antibody.

EXAMPLE 12

Establishment of 3E8/BSM22 Antibody-Expressing Cell Line

A CHO cell line transformed with an expression vector pdCMV-dhfr-3E8/BSM22 was established as described in Example 6 to produce the 3E8/BSM22 antibody.

A clone expressing the 3E8/BSM22 antibody at high concentrations and exhibiting a good growth rate was selected and designated "4D12-B31 cell line", which was deposited at KCTC (Korean Collection for Type Cultures; 52, Oun-dong, Yusong-ku, Taejon, Korea) on May 31, 2004 and assigned accession number KCTC 10646BP.

EXAMPLE 13

Biodistribution and Tumor Targeting of AKA and 3E8 Antibodies

In vivo distribution and tumor targeting of the 3E8 and AKA/HzK antibodies were assessed in athymic mice xenografted with human colon cancer. The purified 3E8 and AKA/HzK antibodies were labeled with a radioisotope, $^{125}$I. TLC (thin layer chromatography) revealed that the $^{125}$I-labeled antibodies have a radiochemical purity of more than 99%. The $^{125}$I-labeled 3E8 or AKA/HzK antibody was intravenously injected into the mouse model, and was assessed for its in vivo distribution 4, 24, 48 and 72 hrs after injection of the antibody. The percent of injected dose per gram of tissue (% ID/g tissue) was determined in cancer and differentiated tissues, and the results are given in FIG. 10 and Table 1, below. Both AKA/HzK (A panel of FIG. 10) and 3E8 (B panel of FIG. 10) targeted cancer. The maximum radioactivity in cancer tissues was achieved 24 hrs after injection of the antibody. At all time points, 3E8 was retained in cancer tissues in higher levels than AKA/HzK. Also, $^{125}$I-3E8 was found to be retained in cancer tissues at high levels for the test period, whereas the accumulation of $^{125}$I-AKA/HzK in cancer tissues decreased in a time-dependent manner. Compared to $^{125}$I-AKA/HzK, the accumulation of $^{131}$I-3E8 in cancer tissues at 24, 48 and 72 hrs postinjection was increased to about 167%, 224% and 236%, respectively. These results indicate that 3E8 has higher affinity for tumors and thus has better binding capacity for tumors than AKA/HzK.

TABLE 1

Biodistribution of $^{125}$I-AKA and $^{125}$I-3E8 in LS174T tumors bearing athymic mice[a]

| Ab | Organ | Time point (h) | | | |
|---|---|---|---|---|---|
| | | 4 | 24 | 48 | 72 |
| AKA | Blood | 16.6 ± 1.4 | 8.0 ± 1.2 | 4.0 ± 2.9 | 2.6 ± 0.6 |
| | Liver | 6.5 ± 1.9 | 3.3 ± 1.2 | 2.0 ± 0.4 | 1.2 ± 0.2 |
| | Lung | 8.4 ± 1.9 | 4.9 ± 0.5 | 2.8 ± 1.3 | 2.1 ± 0.3 |
| | Spleen | 12.2 ± 4.6 | 4.6 ± 1.6 | 3.6 ± 0.5 | 2.4 ± 0.2 |
| | Kidney | 8.2 ± 0.8 | 4.3 ± 0.7 | 1.9 ± 1.2 | 1.3 ± 0.3 |
| | Muscle | 2.2 ± 0.8 | 2.7 ± 0.5 | 3.6 ± 0.9 | 3.8 ± 0.6 |
| | Tumor | 4.0 ± 2.0 | 10.6 ± 2.6 | 7.7 ± 5.8 | 7.2 ± 3.3 |
| 3E8 | Blood | 20.0 ± 0.8 | 13.6 ± 0.3 | 8.9 ± 0.5 | 5.5 ± 3.7 |
| | Liver | 6.3 ± 0.7 | 4.1 ± 0.1 | 2.9 ± 0.2 | 2.3 ± 0.2 |
| | Lung | 9.5 ± 1.5 | 6.1 ± 0.5 | 4.2 ± 1.6 | 3.9 ± 0.8 |
| | Spleen | 6.6 ± 1.2 | 4.2 ± 0.4 | 4.2 ± 1.4 | 3.2 ± 0.6 |
| | Kidney | 8.8 ± 0.5 | 5.6 ± 0.6 | 3.6 ± 0.2 | 3.0 ± 0.6 |
| | Muscle | 2.2 ± 0.4 | 3.1 ± 0.4 | 2.3 ± 0.2 | 2.0 ± 0.4 |
| | Tumor | 7.9 ± 0.9 | 17.7 ± 3.6 | 17.3 ± 1.0 | 17.0 ± 3.6 |

[a]Number of mice/group; n = 3, Data are reported as mean ± SD. The differences in tumor uptakes between AKA and 3E8 were statistically significant for all time points (P < 0.05).

EXAMPLE 14

Evaluation of Radioimmunotherapeutic Efficacy of 3E8

The therapeutic efficacy of the 3E8 antibody was tested by two methods, an assay for inhibitory effect of the antibody on tumor growth and a mouse survival assay. First, to analyze the inhibitory effect of the antibody on tumor growth, $^{131}$I-3E8 (20 mg/7.4 MBq, 200 mCi) was intravenously injected into eight athymic mice bearing human colon cancer xenografts six times (once per week). Eight control mice were injected with unlabeled 3E8 instead of $^{131}$I-3E8. As a result, tumor growth was delayed in mice administered with $^{131}$I-3E8 (FIG. 11). In the treated mice, the tumor doubling time (Td) was 13.2 days, which was remarkably extended compared to the Td (5.6 days) of the control mice (treated with unlabeled 3E8). No large change in body weight was found in tested mice. That is, the body weight of the control mice was slightly increased to about 102% as time went by, and the body weight of the treated mice decreased to 87% of the initial body weight.

To estimate the survival rates of mice treated with $^{131}$I-3E8, seven athymic mice were administered with 7.4 MBq of $^{131}$I-3E8 every week for a total period of 6 weeks. 50% survival rate of mouse treated with $^{131}$I-3E8 extended period of 90.5 days in comparison with the control mice, which survived for a period of 42.5 days. Thus, the treated mice had a 50% survival rate 2.1-fold longer than the control mice (FIG. 12). No large change in body weight was found in tested mice. That is, a slight body weight gain was found in the control mice as time went by, and the treated mice showed an about 10% decrease in body weight.

INDUSTRIAL APPLICABILITY

As described hereinbefore, the present invention provides a humanized antibody which has enhanced antigen binding affinity by mutating a heavy chain of AKA/HzK, and another humanized antibody which has enhanced antigen binding affinity by replacing a light chain of the above humanized antibody with a human light chain. These antibodies and anticancer compositions comprising the same have higher binding affinity for a TAG-72 antigen than does the conventional AKA/HzK antibody, and are capable of more effectively diagnosing and treating cancer than the conventional humanized antibody against TAG-72.

The invention claimed is:

1. An isolated humanized antibody against tumor-associated glycoprotein-72 (TAG-72), which comprises (i) a heavy chain variable region having the amino acid sequence of SEQ ID NO:1, with the exception that amino acid 100 of SEQ ID NO:1 is selected from the group consisting of leucine (Leu) and tryptophan (Trp), amino acid 101 of SEQ ID NO:1 is selected from the group consisting of isoleucine (Ile), valine (Val), leucine (Leu) and alanine (Ala), amino acid 102 of SEQ ID NO:1 is selected from the group consisting of methionine (Met) and glutamine (Gln), and amino acid 103 of SEQ ID NO:1 is selected from the group consisting of alanine (Ala), glutamine (Gln) and glycine (Gly), and (ii) a light chain variable region having the amino acid sequence of SEQ ID NO: 21.

2. The isolated humanized antibody according to claim 1, wherein amino acid 100 of SEQ ID NO:1 is tryptophan (Trp), wherein amino acid 101 of SEQ ID NO:1 is selected from the group consisting of isoleucine (Ile), valine (Val), leucine (Leu) and alanine (Ala), wherein amino acid 102 of SEQ ID NO:1 is selected from the group consisting of methionine (Met) and glutamine (Gln), and wherein amino acid 103 of SEQ ID NO:1 is selected from the group consisting of glutamine (Gln) and glycine (Gly).

3. The isolated humanized antibody according to claim 2, wherein amino acid 100 of SEQ ID NO:1 is tryptophan (Trp), wherein amino acid 101 of SEQ ID NO:1 is selected from the group consisting of isoleucine (Ile) and valine (Val), wherein amino acid 102 of SEQ ID NO:1 is methionine (Met), and wherein amino acid 103 of SEQ ID NO:1 is glutamine (Gln).

4. The isolated humanized antibody according to claim 1, wherein the amino acid sequence of the heavy chain variable region is selected from the group consisting of amino acid sequences of SEQ ID NOS: 2 to 6.

5. An isolated humanized antibody against tumor-associated glycoprotein-72 (TAG-72), which comprises (i) a heavy chain variable region having the amino acid sequence of SEQ ID NO:1, with the exception that amino acid 100 of SEQ ID NO:1 is selected from the group consisting of leucine (Leu) and tryptophan (Trp), amino acid 101 of SEQ ID NO:1 is selected from the group consisting of isoleucine (Ile), valine (Val), leucine (Leu) and alanine (Ala), amino acid 102 of SEQ ID NO:1 is selected from the group consisting of methionine (Met) and glutamine (Gln), and amino acid 103 of SEQ ID NO:1 is selected from the group consisting of alanine (Ala), glutamine (Gln) and glycine (Gly), and (ii) a light chain variable region having the amino acid sequence of SEQ ID NO:22.

6. The isolated humanized antibody according to claim 5, wherein amino acid 100 of SEQ ID NO:1 is tryptophan (Trp), wherein amino acid 101 of SEQ ID NO:1 is selected from the group consisting of isoleucine (Ile), valine (Val), leucine (Leu) and alanine (Ala), wherein amino acid 102 of SEQ ID NO:1 is selected from the group consisting of methionine (Met) and glutamine (Gln), and wherein amino acid 103 of SEQ ID NO:1 is selected from the group consisting of glutamine (Gln) and glycine (Gly).

7. The isolated humanized antibody according to claim 6, wherein amino acid 100 of SEQ ID NO:1 is tryptophan (Trp), wherein amino acid 101 of SEQ ID NO:1 is selected from the group consisting of isoleucine (Ile) and valine (Val), wherein amino acid 102 of SEQ ID NO:1 is methionine (Met), and wherein amino acid 103 of SEQ ID NO:1 is glutamine (Gln).

8. The isolated humanized antibody according to claim 5, wherein the amino acid sequence of the heavy chain variable region is selected from the group consisting of amino acid sequences of SEQ ID NOS:2 to 6.

9. The isolated humanized antibody according to claim 8, wherein the amino acid sequence of the heavy chain variable region is set forth in SEQ ID NO:4.

10. An anticancer composition for the treatment of colon cancer in a human subject in need thereof, wherein the antibody comprises a heavy chain variable region having the amino acid sequence of SEQ ID NO:4 and a light chain variable region having the amino acid sequence SEQ ID NO:21.

* * * * *

SEQUENCE LISTING

<160> NUMBER OF SEQ ID NOS: 37

<210> SEQ ID NO 1
<211> LENGTH: 115
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
            100                 105                 110

Val Ser Ser
        115

<210> SEQ ID NO 2
<211> LENGTH: 115
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Val Gln Gly Tyr Trp Gly Gln Gly Thr Leu Val Thr
            100                 105                 110

Val Ser Ser
        115

<210> SEQ ID NO 3
<211> LENGTH: 115
<212> TYPE: PRT
<213> ORGANISM: Artificial Sequence
<220> FEATURE:
<223> OTHER INFORMATION: Synthetic

```
<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Leu Ile Gln Gly Tyr Trp Gly Gln Gly Thr Leu Val Thr
            100                 105                 110

Val Ser Ser
        115

<210> SEQ ID NO 4
<211> LENGTH: 115
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Trp Ile Met Gln Tyr Trp Gly Gln Gly Thr Leu Val Thr
            100                 105                 110

Val Ser Ser
        115

<210> SEQ ID NO 5
<211> LENGTH: 115
<212> TYPE: PRT
<213> ORGANISM: Artificial Sequence
<220> FEATURE:
<223> OTHER INFORMATION: Synthetic

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
```

```
            50                  55                  60
Gln Gly Arg Val Thr Ile Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Val Met Ala Tyr Trp Gly Gln Gly Thr Leu Val Thr
            100                 105                 110

Val Ser Ser
        115

<210> SEQ ID NO 6
<211> LENGTH: 115
<212> TYPE: PRT
<213> ORGANISM: Artificial Sequence
<220> FEATURE:
<223> OTHER INFORMATION: Synthetic

<400> SEQUENCE: 6

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp His
                 20                  25                  30

Ala Ile His Trp Val Arg Gln Ala Pro Gly Gln Arg Leu Glu Trp Met
             35                  40                  45

Gly Tyr Phe Ser Pro Gly Asn Asp Asp Phe Lys Tyr Ser Gln Lys Phe
     50                  55                  60

Gln Gly Arg Val Thr Ile Thr Ala Asp Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Ile Met Ala Tyr Trp Gly Gln Gly Thr Leu Val Thr
            100                 105                 110

Val Ser Ser
        115

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
aggtgcagct gctcgagtct gg                                      22

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
tcttgcacag taatagaccg ccgtgtc                                 27

<210> SEQ ID NO 9
<211> LENGTH: 54
<212> TYPE: DNA
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 9
gtctattact gtgcaagann snnsnnsnns nnstactggg gccaaggcac tctg      54

<210> SEQ ID NO 10
<211> LENGTH: 17
<212> TYPE: DNA
<213> ORGANISM: Artificial Sequence
<220> FEATURE:
<223> OTHER INFORMATION: Synthetic

<400> SEQUENCE: 10
caccggttcg gggaagt                                               17

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
gacgaattca ctctaaccat ggaa                                       24

<210> SEQ ID NO 12
<211> LENGTH: 24
<212> TYPE: DNA
<213> ORGANISM: Artificial Sequence
<220> FEATURE:
<223> OTHER INFORMATION: Synthetic

<400> SEQUENCE: 12
agactgcaca agctggacct ggga                                       24

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
cagctagtgc agtctggggc tgaag                                      25

<210> SEQ ID NO 14
<211> LENGTH: 24
<212> TYPE: DNA
<213> ORGANISM: Artificial Sequence
<220> FEATURE:
<223> OTHER INFORMATION: Synthetic
```

<400> SEQUENCE: 14
gtactgcatg atccacgatc ttgc                                          24

<210> SEQ ID NO 15
<211> LENGTH: 25
<212> TYPE: DNA
<213> ORGANISM: Artificial Sequence
<220> FEATURE:
<223> OTHER INFORMATION: Synthetic

<400> SEQUENCE: 15
tggatcatgc agtactgggg ccaag                                         25

<210> SEQ ID NO 16
<211> LENGTH: 345
<212> TYPE: DNA
<213> ORGANISM: Artificial Sequence
<220> FEATURE:
<223> OTHER INFORMATION: Synthetic

<400> SEQUENCE: 16
caggtccagc tagtgcagtc tggggctgaa gtgaagaagc ctggggcttc agtgaaggtg    60
tcctgcaagg cttctggcta caccttcact gaccatgcaa ttcactgggt gcgccaggcc   120
cctggacaac gccttgagtg gatgggatat ttttctcctg gcaacgatga ttttaaatac   180
tcccagaagt tccagggacg cgtgacaatc actgcagaca aatccgcgag cacagcctac   240
atggagctga gcagcctgag atctgaggac acggcggtct attactgtgc aagaagcctg   300 gtgcagggt actggggcca aggactctg gtcactgtct cttca                    345

<210> SEQ ID NO 17
<211> LENGTH: 345
<212> TYPE: DNA
<213> ORGANISM: Artificial Sequence
<220> FEATURE:
<223> OTHER INFORMATION: Synthetic

<400> SEQUENCE: 17
caggtccagc tagtgcagtc tggggctgaa gtgaagaagc ctggggcttc agtgaaggtg    60
tcctgcaagg cttctggcta caccttcact gaccatgcaa ttcactgggt gcgccaggcc   120
cctggacaac gccttgagtg gatgggatat ttttctcctg gcaacgatga ttttaaatac   180
tcccagaagt tccagggacg cgtgacaatc actgcagaca aatccgcgag cacagcctac   240
atggagctga gcagcctgag atctgaggac acggcggtct attactgtgc aagatcgttg   300
atccaggggt actggggcca aggactctg gtcactgtct cttca                   345

<210> SEQ ID NO 18
<211> LENGTH: 345
<212> TYPE: DNA
<213> ORGANISM: Artificial Sequence
<220> FEATURE:
<223> OTHER INFORMATION: Synthetic

<400> SEQUENCE: 18
caggtccagc tagtgcagtc tggggctgaa gtgaagaagc ctggggcttc agtgaaggtg    60
tcctgcaagg cttctggcta caccttcact gaccatgcaa ttcactgggt gcgccaggcc   120
cctggacaac gccttgagtg gatgggatat ttttctcctg gcaacgatga ttttaaatac   180
tcccagaagt tccagggacg cgtgacaatc actgcagaca aatccgcgag cacagcctac   240
atggagctga gcagcctgag atctgaggac acggcggtct attactgtgc aagatcgtgg   300
atcatgcagt actggggcca agggactctg gtcactgtct cttca      345

<210> SEQ ID NO 19
<211> LENGTH: 345
<212> TYPE: DNA
<213> ORGANISM: Artificial Sequence
<220> FEATURE:
<223> OTHER INFORMATION: Synthetic

<400> SEQUENCE: 19
caggtccagc tagtgcagtc tggggctgaa gtgaagaagc ctggggcttc agtgaaggtg      60
tcctgcaagg cttctggcta caccttcact gaccatgcaa ttcactgggt gcgccaggcc     120
cctggacaac gccttgagtg gatgggatat ttttctcctg caacgatga ttttaaatac      180
tcccagaagt tccagggacg cgtgacaatc actgcagaca atccgcgag cacagcctac      240
atggagctga gcagcctgag atctgaggac acggcggtct attactgtgc aagaagcctg     300
gtgatggcat actggggcca agggactctg gtcactgtct cttca                    345

<210> SEQ ID NO 20
<211> LENGTH: 345
<212> TYPE: DNA
<213> ORGANISM: Artificial Sequence
<220> FEATURE:
<223> OTHER INFORMATION: Synthetic

<400> SEQUENCE: 20
caggtccagc tagtgcagtc tggggctgaa gtgaagaagc ctggggcttc agtgaaggtg      60
tcctgcaagg cttctggcta caccttcact gaccatgcaa ttcactgggt gcgccaggcc     120
cctggacaac gccttgagtg gatgggatat ttttctcctg caacgatga ttttaaatac      180
tcccagaagt tccagggacg cgtgacaatc actgcagaca atccgcgag cacagcctac      240
atggagctga gcagcctgag atctgaggac acggcggtct attactgtgc aagaagcctg     300
atcatggcat actggggcca agggactctg gtcactgtct cttca                    345

<210> SEQ ID NO 21
<211> LENGTH: 113
<212> TYPE: PRT
<213> ORGANISM: Artificial Sequence
<220> FEATURE:
<223> OTHER INFORMATION: Synthetic

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys

```
<210> SEQ ID NO 22
<211> LENGTH: 113
<212> TYPE: PRT
<213> ORGANISM: Homo sapiens
<220> FEATURE:
<221> NAME/KEY: MISC_FEATURE
<222> LOCATION: (1)..(113)
<223> OTHER INFORMATION: light chain variable region of 3E8/BSM22

<400> SEQUENCE: 22

Asp Ile Val Met Thr Gln Ser Pro Asp Ser Leu Ala Val Ser Leu Gly
1               5                   10                  15

Glu Arg Ala Thr Ile His Cys Lys Ser Ser Gln Ser Ile Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Leu Tyr Trp Ala Ser Thr Arg Glu Ala Gly Val
    50                  55                  60

Pro Asp Arg Phe Ser Gly Gly Gly Ser Gly Thr Asp Phe Thr Leu Thr
65                  70                  75                  80

Ile Ser Ser Leu Gln Pro Glu Asp Ser Ala Thr Tyr Tyr Cys Gln Gln
                85                  90                  95

Tyr Asn Thr Tyr Pro Leu Thr Phe Gly Gly Gly Thr Lys Val Glu Ile
            100                 105                 110

Lys

<210> SEQ ID NO 23
<211> LENGTH: 339
<212> TYPE: DNA
<213> ORGANISM: Homo sapiens
<220> FEATURE:
<221> NAME/KEY: misc_feature
<222> LOCATION: (1)..(339)
<223> OTHER INFORMATION: DNA sequence coding for variable region of
      3E8/BSM22

<400> SEQUENCE: 23
gacatcgtga tgactcagtc tccagactcc ctggctgtgt ctctgggcga gagggccacc      60
atccactgca agtccagcca gagtatttta tacagctcca acaataagaa ctacttagct     120
tggtatcaac agaaaccagg acagcctccc aagttgctcc tttactgggc atctacccgg     180
gaagccgggg tccctgaccg tttcagtggc ggcgggtctg gacagatttc actctcacc      240 atcagcagcc tgcagcctga agattctgca acttattact gccaacagta taatacttac     300
ccgctcactt tcggcggagg gaccaaggtg gagatcaaa                            339

<210> SEQ ID NO 24
<211> LENGTH: 58
<212> TYPE: DNA
<213> ORGANISM: Artificial Sequence
<220> FEATURE:
<223> OTHER INFORMATION: Synthetic

<400> SEQUENCE: 24
gcgccgtcta gaattaacac tctcccctgt tgaagctctt tgtgacgggc gaactcag       58

<210> SEQ ID NO 25
<211> LENGTH: 38
<212> TYPE: DNA
<213> ORGANISM: Artificial Sequence
<220> FEATURE:
<223> OTHER INFORMATION: Synthetic

<400> SEQUENCE: 25
```

```
gagccgcacg agcccgagct ccagatgacc cagtctcc                              38

<210> SEQ ID NO 26
<211> LENGTH: 38
<212> TYPE: DNA
<213> ORGANISM: Artificial Sequence
<220> FEATURE:
<223> OTHER INFORMATION: Synthetic

<400> SEQUENCE: 26
gagccgcacg agcccgagct cgtgatgacc cagtctcc                              38

<210> SEQ ID NO 27
<211> LENGTH: 38
<212> TYPE: DNA
<213> ORGANISM: Artificial Sequence
<220> FEATURE:
<223> OTHER INFORMATION: Synthetic

<400> SEQUENCE: 27
gagccgcacg agcccgagct cgtgwtgacv cagtctcc                              38

<210> SEQ ID NO 28
<211> LENGTH: 38
<212> TYPE: DNA
<213> ORGANISM: Artificial Sequence
<220> FEATURE:
<223> OTHER INFORMATION: Synthetic

<400> SEQUENCE: 28
gagccgcacg agcccgagct cgtgatgact cagtctcc                              38

<210> SEQ ID NO 29
<211> LENGTH: 38
<212> TYPE: DNA
<213> ORGANISM: Artificial Sequence
<220> FEATURE:
<223> OTHER INFORMATION: Synthetic

<400> SEQUENCE: 29
gagccgcacg agcccgagct cacactcacg cagtctcc                              38

<210> SEQ ID NO 30
<211> LENGTH: 21
<212> TYPE: DNA
<213> ORGANISM: Artificial Sequence
<220> FEATURE:
<223> OTHER INFORMATION: Synthetic

<400> SEQUENCE: 30
tgcaaagctt cggcacgagc a                                                21

<210> SEQ ID NO 31
<211> LENGTH: 17
<212> TYPE: DNA
<213> ORGANISM: Artificial Sequence
<220> FEATURE:
<223> OTHER INFORMATION: Synthetic

<400> SEQUENCE: 31
gcagccaccg tacgttt                                                     17

<210> SEQ ID NO 32
<211> LENGTH: 38
<212> TYPE: DNA
<213> ORGANISM: Artificial Sequence
```

```
<220> FEATURE:
<223> OTHER INFORMATION: Synthetic

<400> SEQUENCE: 32
tctggtgttg aaggagacac tgtgatgacc cagtctcc                              38

<210> SEQ ID NO 33
<211> LENGTH: 17
<212> TYPE: DNA
<213> ORGANISM: Artificial Sequence
<220> FEATURE:
<223> OTHER INFORMATION: Synthetic

<400> SEQUENCE: 33
gtctccttca acaccag                                                     17

<210> SEQ ID NO 34
<211> LENGTH: 38
<212> TYPE: DNA
<213> ORGANISM: Artificial Sequence
<220> FEATURE:
<223> OTHER INFORMATION: Synthetic

<400> SEQUENCE: 34
tctggtgttg aaggagacat ccagatgacc cagtctcc                              38

<210> SEQ ID NO 35
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is Leu or Trp
<220> FEATURE:
<221> NAME/KEY: MISC_FEATURE
<222> LOCATION: (2)..(2)
<223> OTHER INFORMATION: Xaa is Ala, Ile, Leu, or Val
<220> FEATURE:
<221> NAME/KEY: MISC_FEATURE
<222> LOCATION: (3)..(3)
<223> OTHER INFORMATION: Xaa is Gln or Met
<220> FEATURE:
<221> NAME/KEY: MISC_FEATURE
<222> LOCATION: (4)..(4)
<223> OTHER INFORMATION: Xaa is Ala, Gln, or Gly

<400> SEQUENCE: 35

Xaa Xaa Xaa Xaa
1

<210> SEQ ID NO 36
<211> LENGTH: 4
<212> TYPE: PRT
<213> ORGANISM: Artificial Sequence
<220> FEATURE:
<223> OTHER INFORMATION: Synthetic

<400> SEQUENCE: 36

Glu Val Gln Leu
1

<210> SEQ ID NO 37
<211> LENGTH: 4
<212> TYPE: PRT
<213> ORGANISM: Artificial Sequence
<220> FEATURE:
<223> OTHER INFORMATION: Synthetic
```

```
<400> SEQUENCE: 37

Gln Val Gln Leu
1
```